United States Patent [19]

Witte et al.

[11] Patent Number: 4,616,086

[45] Date of Patent: Oct. 7, 1986

[54] PIPERAZINE-SUBSTITUTED ARYL AND ARALKYL CARBOXYLIC ACIDS USEFUL FOR TREATING INFIRMATIES CAUSED BY EXCESS LIPIDS OR THROMBOCYTE

[75] Inventors: Ernst-Christian Witte, Mannheim; Hans P. Wolff, Hirschberg-Grosssachsen; Bernd Hagenbruch, Lampertheim; Karlheinz Stegmeir, Heppenheim; Johannes Pill, Leimen, all of Fed. Rep. of Germany

[73] Assignee: Boehringer Mannheim GmbH, Mannheim, Fed. Rep. of Germany

[21] Appl. No.: 657,032

[22] Filed: Oct. 1, 1984

Related U.S. Application Data

[63] Continuation of Ser. No. 422,638, Sep. 24, 1982, abandoned.

[30] Foreign Application Priority Data

Oct. 8, 1981 [DE] Fed. Rep. of Germany ....... 3139970

[51] Int. Cl.$^4$ ................. C07D 241/04; A61K 31/495
[52] U.S. Cl. .................................... 544/383; 544/393; 544/395; 544/398; 544/399; 544/400; 514/255
[58] Field of Search ............... 544/383, 386, 389, 392, 544/393, 394, 399, 395, 398, 400; 514/225, 255

[56] References Cited

U.S. PATENT DOCUMENTS

| 3,448,192 | 6/1969 | Mauwernay | 544/399 |
| 3,641,040 | 2/1972 | Carney | 544/394 |
| 3,910,916 | 10/1975 | Protiva et al. | 544/392 |

FOREIGN PATENT DOCUMENTS

| 330157 | 6/1976 | Austria . |
| 788850 | 9/1972 | France . |
| 7016097 | 11/1970 | Netherlands . |
| 1382606 | 2/1975 | United Kingdom . |
| 2033890 | 5/1980 | United Kingdom . |
| 2091729 | 8/1982 | United Kingdom . |

OTHER PUBLICATIONS

Medicinal Chemistry, Alfred Burger, p. 42, col. 2, last paragraph.
Hansl, N., Chem. Abstract, vol. 80, 1974, p. 353, 82431e, Alkyl m-(2-aminoethyl)benzoates.
Cazin et al, Chem. Abstract, vol. 94, 1981, p. 25, 57963m, In Vitro Study of the Inhibitory Effect of Various β-Aminoketones on Platelet Aggregation.
Cazin, Publ., Acta Therapeutica 6 (1980).

Primary Examiner—Donald G. Daus
Assistant Examiner—Cecilia Shen
Attorney, Agent, or Firm—Felfe & Lynch

[57] ABSTRACT

The present invention is concerned with new carboxylic acid derivatives, with processes for the preparation thereof and with pharmaceutical compositions for lipid depression and thrombocyte aggregation, containing them, and to methods for treating infirmaties caused by excess lipids or thrombocyte aggregation.

The new carboxylic acid derivatives according to the present invention are compounds of the general formula:

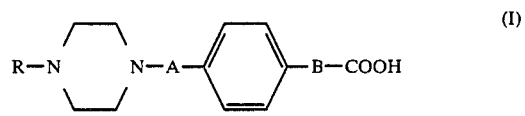

(I)

wherein A is a valency bond or a lower alkylene chain, B is a valency bond or a saturated or unsaturated lower alkylene chain, R is hydrogen, an alkyl group which can be substituted by hydroxyl, carboxyl, sulphonic acid or optionally substituted phenoxy group, or R is an aralkyl radical, the aryl moiety of which can be substituted and the alkyl moiety of which is optionally unsaturated and can contain up to 4 carbon atoms, or R is a phenacyl radical, the phenyl moiety optionally substituted, or R is an acyl radical derived from aliphatic, araliphatic or aromatic carboxylic or sulphonic acid, or R is an aryl radical optionally substituted with the proviso that when A is a valency bond, R cannot be hydrogen, methyl, ethyl, hydroxyethyl, benzyl or phenyl, and the physiologically acceptable salts, esters and amides thereof.

22 Claims, No Drawings

PIPERAZINE-SUBSTITUTED ARYL AND ARALKYL CARBOXYLIC ACIDS USEFUL FOR TREATING INFIRMATIES CAUSED BY EXCESS LIPIDS OR THROMBOCYTE

This application is a continuation of application Ser. No. 422,638, filed 9/24/82, now abandoned.

The present invention is concerned with new carboxylic acid derivatives, with processes for the preparation thereof and with pharmaceutical compositions for lipid depression and thrombocyte aggregation, containing them, and to methods for treating infirmaties caused by excess lipids or thrombocyte aggregation.

The new carboxylic acid derivatives according to the present invention are compounds of the general formula:

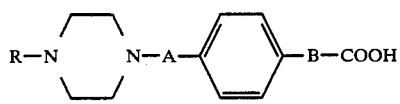

wherein A is a valency bond or a divalent lower alkylene chain, B is a valency bond or a divalent saturated or unsaturated lower aliphatic chain and R is a hydrogen atom or a straight-chained or branched alkyl radical, which can be substituted one or more times by hydroxyl, carboxyl, sulphonic acid or phenoxy, the phenoxy radical optionally being substituted one or more times by lower alkyl, lower alkoxy, halogen, nitro, cyano, carboxyl or acylamino; or R is an aralkyl radical, the aryl moiety of which is optionally substituted one or more times by halogen, hydroxyl, lower alkoxy, cyano, carboxyl, nitro, acylamino, lower alkyl or trifluoromethyl and the alkyl moiety of which is optionally unsaturated and can contain up to 4 carbon atoms; or R is a phenacyl radical, the phenyl moiety of which can be substituted one or more times by halogen, hydroxyl or lower alkyl; or R is an acyl radical derived from an aliphatic, araliphatic or aromatic carboxylic or sulphonic acid, the aryl moiety of which can be substituted one or more times by halogen, hydroxyl or lower alkyl groups; or R is an aryl radical, which is optionally substituted by halogen, trifluoromethyl, phenyl, phenoxy, benzyloxy, 4-chlorobenzoyl or 4-chlorophenoxy, with the proviso that, when A is a valency bond, R is not a hydrogen atom or a methyl, ethyl, hydroxyethyl, benzyl or phenyl radical; as well as the physiologically acceptable salts, esters and amides thereof.

Austrian Patent Specification No. 330,157 [C.A. 85, 1976, 192404 j] describes 3-N-piperazinylalkylbenzoic acids which can be used as muscle relaxants and for increasing the memory capacity.

Similar compounds have also been described as spasmolytics in British Patent Specification No. 1,382,606 [C.A. 83, 1975, 27946 p] and in South African Patent Specification No. 72.06378 [C.A. 80, 1974, 82431 e].

Further, U.S. Pat. No. 3,641,040 describes piperazinylphenyl-acetic acids, the piperazine moiety of which can be substituted by methyl, ethyl, 2-hydroxyethyl, benzyl or phenyl radicals. However, these compounds possess an inflammation-inhibiting activity.

The new compounds of general formula (I) and the physiologically acceptable salts, esters and amides thereof display not only an excellent lipid-sinking action but also a marked inhibiting action on the thrombocyte aggregation.

When the substituent R is an alkyl radical, this is to be understood to be a straight-chained or branched chain radical containing up to 16 carbon atoms, preferred radicals including methyl, ethyl and hexadecyl radicals. Preferred substituted alkyl radicals include 2-hydroxypropyl, 1-carboxyethyl and 3-propyl-1-sulphonic acid radicals. In the case of an alkyl radical substituted by a phenoxy radical, it is preferably a 2-phenoxyethyl or 2-phenoxypropyl radical, which is optionally substituted by a $C_1$–$C_6$ alkyl radical, especially a methyl radical, a $C_1$–$C_6$ alkoxy radical, especially a methoxy radical, halogen (whereby here and in all other cases halogen is to be understood to mean fluorine, chlorine, bromine and iodine), nitro, cyano or carboxyl.

When the substituent R is an aralkyl radical, it is preferably a benzyl, phenethyl, 3-phenylpropyl or 2-benzylpropyl radical. In these compounds, the aromatic ring can be substituted one or more times, the substituents being halogen (as defined above), $C_1$–$C_6$ alkoxy, preferably methoxy, hydroxy, or $C_1$–$C_6$ alkyl, preferably tert.-butyl, as well as trifluoromethyl.

When R is an aralkenyl radical, it is preferably a cinnamyl radical or an α- or β-methylcinnamyl radical. Substituents of the phenyl ring include halogen (as defined above), $C_1$–$C_6$ alkoxy, especially methoxy, cyano carboxyl, nitro, $C_1$–$C_6$ acylamino, especially acetylamino, as well as trifluoromethyl.

R can also be a phenacyl radical, which is to be understood to mean, in particular, 4-chlorobenzoylmethyl or 1-[4-hydroxy-3,5-di-(tert.-butyl)-benzoyl]ethyl.

When R is an acyl radical, this is an acid residue of an aliphatic, araliphatic or aromatic carboxylic or sulphonic acid. In the case of the aliphatic and araliphatic acyl radicals, the alkylene moiety can be straight-chained or branched and saturated or unsaturated.

Preferred acyl radicals derived from carboxylic acids include 2-methyl-3-phenylpropionyl, 3-phenylpropionyl, cinnamoyl, phenacyl and benzoyl, the phenyl radical optionally being substituted one or more times preferably by halogen, especially chlorine, hydroxyl or $C_1$–$C_6$ alkyl, preferably tert.-butyl.

Preferred acyl radicals derived from sulphonic acids include residues of methanesulphonic acid, benzenesulphonic acid and phenacylsulphonic acid. In the last two cases, the aryl radicals are preferably substituted by halogen, especially chlorine, or by $C_1$–$C_6$ alkyl, especially methyl.

When the substituent R is an aryl radical, this is preferably a 4-chlorophenyl, 3-trifluoromethylphenyl, 4-(4-chlorobenzoyl)-phenyl, 4-biphenylyl, 4-phenoxyphenyl or 4-benzyloxyphenyl radical.

In general formula (I), A is either a valency bond or, for example, one of the radicals —CH$_2$—, —(CH$_2$)$_2$— or —(CH$_2$)$_3$— (unbranched) or one of the radicals

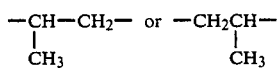

(branched).

B is either a valency bond or, for example, one of the radicals —CH$_2$—, —(CH$_2$)$_2$—,

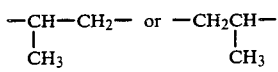

(saturated) or one of the radicals —CH=CH—,

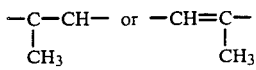

(unsaturated).

The esters derived from the carboxylic acids of the general formula (I) contain, as alcohol component, a lower monohydroxy alcohol, of which methanol, ethanol and n-butanol are preferred, or a polyhydroxy alcohol, for example glycerol, or an alcohol containing additional functional groups, for example ethanolamine or a glycol ether.

The amides according to the present invention derived from the carboxylic acids of general formula (I) contain, as amine component, for example ammonia, p-aminobenzoic acid, β-alanine, ethanolamine or 2-aminopropanol, those previously mentioned being preferred. However, there can also be considered alkylamines, for example isopropylamine or tert.-butylamine, dialkylamines, such as diethylamine, as well as cyclic amines, for example morpholine or 4-alkyl-, -aralkyl- or -arylpiperazines, such as 4-methylpiperazine, 4-(4-chlorobenzyl)-piperazine or 4-(3-methoxyphenyl)-piperazine.

The above definition of the compounds according to the present invention are also to include all possible stereoisomers, as well as mixtures thereof.

The present invention also provides processes for the preparation of carboxylic acids of general formula (I), wherein (a) a compound of the general formula:

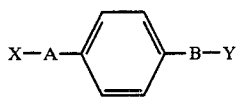

(II)

is either reacted with an $N_1$-protected piperazine and, after splitting off of the protective group, the substituent R is introduced by alkylation or acylation, or is reacted with a piperazine already monosubstituted by R; or (b) a compound of the general formula:

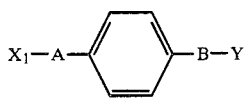

(III)

is reacted with a compound of the general formula:

(IV)

whereby one of the symbols $X_1$ and $X_2$ signifies an $NH_2$ group and the other represents a

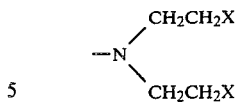

radical, and, in the above two processes, A and R have the same meanings as above, X is a reactive residue, B is a valency bond, a saturated or unsaturated lower alkylene chain or a residue convertible into this group and Y is an acid amide or —$COOR_2$ group, in which $R_2$ is a hydrogen atom or a lower alkyl radical or represents a residue convertible into these groups, whereafter, if desired, the compound obtained is converted into a free carboxylic acid or into a salt, ester or amide thereof and a group B is, if desired, converted into a saturated or unsaturated lower alkyl chain or the residue R is replaced by another residue R.

Process (a) is preferably employed for the preparation of compounds of general formula (I) in which A is an alkylene chain, whereas process (b) is, as a rule, used for the preparation of compounds in which A is a valency bond and R is an optionally substituted aryl radical.

The subsequent conversion of the group —B—Y in the products according to processes (a) and (b) can be carried out in various ways. Thus, for example, a compound of the general formula:

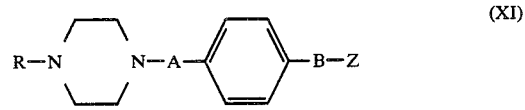

(XI)

in which R, A and B have the same meanings as above and Z is a residue convertible by oxidation into a carboxyl function, is oxidised.

Further processes include the reduction of a compound of the general formula:

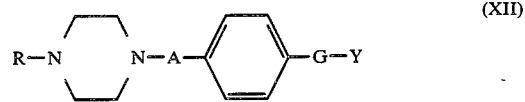

(XII)

in which G represents a carbon chain which contains one of the groups

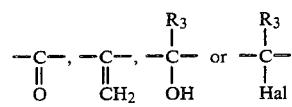

or optionally functional derivatives of these groups, or, when B represents an unbranched chain, reaction of a compound of the general formula:

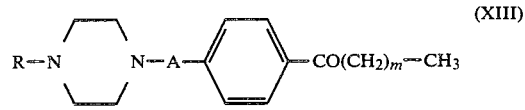

(XIII)

in which m is 0, 1 or 2, under the conditions of an optionally modified Willgerodt-Kindler reaction.

For the preparation of compounds of the general formula:

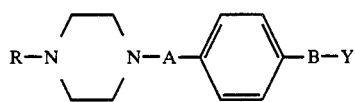

(XIV)

in which B has the special meaning of

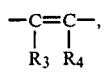

in which $R_3$ and $R_4$ are the same or different and each signifies a hydrogen atom or a lower alkyl radical, there can be used all processes conventionally employed for the preparation of cinnamic acid and of its derivatives:

(1) When compounds (XIV) are available in which B has the meaning

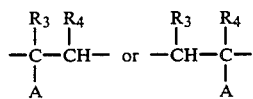

wherein A is a halogen atom, a hydroxyl group or a functionally changed hydroxyl group, the desired compounds (XIV), in which B represents the group:

are obtained by the action of an agent splitting off HA.

(2) When compounds are available of the general formula:

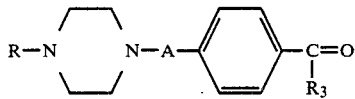

(XV)

the desired cinnamic acid derivatives can be prepared by an aldol condensation, i.e. by reaction with activated CH groups. Such compounds include, for example, acetic acid and its derivatives and especially malonic acid derivatives of the general formula:

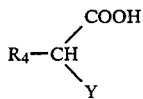

(XVI)

whereby, in the latter case, after condensation has taken place, a decarboxylation occurs.

As a further possibility of such aldol-like reactions, there may be mentioned the Perkin reaction, which consists in a reaction of compounds of general formula (XV) with the anhydride of an aliphatic carboxylic acid in the presence of an alkali metal salt, optionally of the same carboxylic acid.

(3) A third possibility consists in the reaction of compounds of general formula (XV) with appropriate organophosphorus compounds in the manner of modified Wittig reactions. Examples of such organophosphorus reaction components include the alkoxycarbonylmethylphosphonic acid alkyl esters of the general formula:

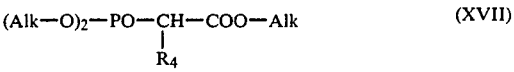

(XVII)

By hydrogenation of the cinnamic acid derivatives obtained according to methods 1 to 3 or by other methods, there can be prepared the analogous compounds with a saturated carbon chain.

It is clear that the above-described methods cannot be employed when R contains groups which prevent these methods or are sensitive towards these methods. In such cases, the piperazine is temporarily protected. The protected compound (R'=protective group)

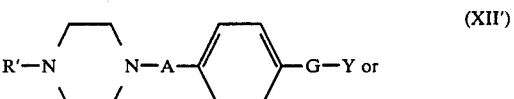

(XII')

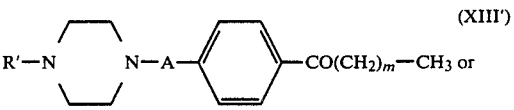

(XIII')

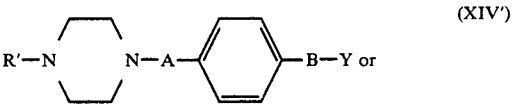

(XIV')

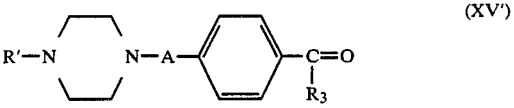

(XV')

are then reacted, the protective group R' is removed by appropriate methods and the desired group R is then introduced by alkylation or acylation, for example according to process (a).

In the case of alkylation according to process (a), when R is alkyl, aralkyl, aralkenyl or phenacyl, as reactive derivative there is used either a halide, especially a chloride or bromide, or an appropriate sulphonic acid ester, for example a mesylate or tosylate. The reaction of the halide or sulphonic acid ester with the piperazine is preferably carried out with the addition of an acid-binding agent, for example sodium hydrogen carbonate, sodium carbonate or potassium carbonate. However, this function can also be undertaken by an organic base, for example pyridine or triethylamine, or use is made of a second mole of the piperazine employed. As inert solvent, there can be used, for example, diethyl ether, benzene, tetrahydrofuran, dioxan, methylene chloride or an excess of tertiary amine. When using an inorganic acid binder, the reaction medium can be, for example, ethanol, butan-2-one, dimethylformamide, hexamethylphosphoric acid triamide (HMPT) or acetonitrile.

As reactive derivatives of carboxylic acids in the case of process (a), acid chlorides are especially preferred. However, their esters, azides, anhydrides and mixed anhydrides can also be used just as well. The reaction with a piperazine can, in the case of aromatic acid halides, also be carried out according to the Schotten-Baumann reaction. If it is desired to work under anhydrous conditions, then anhydrous pyridine is preferably used. However, use can also be made of other tertiary bases, for example dimethylaniline or triethylamine, in an inert solvent, for example methylene chloride. Instead of the free piperazino compound, use can also be made of its salts.

For the acylation of the piperazines, there can also be used the free acids if, by means of azeotropic distillation, care is taken to remove the water of reaction formed from the reaction mixture.

To the reaction mixture there can optionally be added catalytically-acting amounts of a tertiary amine, for example triethylamine or dimethylaniline and of the complex of a Lewis acid, for example a boron trifluoride-diethyl ether complex.

As reactive derivatives of the sulphonic acids in the case of process (a), there are preferably used the halides, as well as the esters. As acid-binding agents there are here used, for example, alkali metal acetates, sodium hydrogen carbonate, potassium carbonate, sodium phosphate, calcium oxide, calcium carbonate or magnesium carbonate, and as reaction medium, there can be used, for example, water, aqueous ethanol or aqueous dioxan. If, because of sensitivity to hydrolysis, aqueous media are to be avoided, here, too, use can be made of tertiary organic amines, for example pyridine or triethylamine, optionally in an inert solvent, for example methylene chloride.

For the reaction of compounds of general formula (II) with piperazine derivatives according to process (a), it is preferable to use compounds in which X is a halogen atom, for example bromine or chlorine, or an alkyl or arylsulphonyloxy radical, for example a mesyloxy or tosyloxy radical.

For the reaction of a compound (III) with a compound (IV) according to process (b), there are especially preferred those compounds (IV) in which R is an optionally substituted aryl radical and X is either a chlorine or bromine atom or an alcohol residue esterified with a sulphonic acid, for example X is a mesyloxy or tosyloxy radical. The reaction is preferably carried out in alcohol, for example n-butanol, in the presence of an acid-bonding agent, for example anhydrous potassium carbonate. However, other solvents can also be used, for example dioxan, dimethylformamide or the like.

As oxidizable group for subsequent conversion into a carboxyl function, there is preferably used the hydroxymethyl, aminomethyl or formyl radical and possibly also the acetyl radical or a functional derivative of these radicals. The oxidation can be carried out with the use of the usual oxidation agents, for example manganese-IV compounds, permanganates or dichromates, in the case of the formyl radical, also with atmospheric oxygen or silver oxide and in the case of the acetyl radical, on the other hand, with hypobromite.

For the reduction of a group G present in compounds of the general formula (XII), numerous processes can be used. The reduction of the —CO— group can be carried out, for example, by a Clemmensen reaction using zinc/hydrochloric acid. However, reduction with hydrogen at atmospheric pressure or under an increased pressure in the presence of a metal catalyst, for example palladium or platinum, in a solvent, for example acetic acid or a lower alcohol, is preferred.

The groups

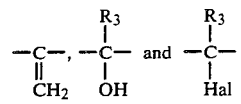

are also preferably reduced by catalytically activated hydrogen, a group containing one hydroxyl group best being reduced in the presence of a strong acid, the presence of sulphuric acid or perchloric acid in catalytic amounts hereby being preferred. It is also possible to reduce with a complex metal hydride, sodium borohydride being preferably employed. In this case, the reaction can be carried out in an alcohol, especially in methanol, or in dioxan or in an aqueous alkaline medium.

The ketones used of general formula (XIII) can easily be prepared by a Friedel-Crafts acylation. They are reacted with sulphur and a secondary amine, preferably with morpholine. The thiomorpholide resulting in the case of this Willgerodt-Kindler reaction is saponified to the carboxylic acid in known manner with the help of an aqueous solution of a strong alkali or with concentrated hydrochloric acid or also with a mixture of sulphuric acid, glacial acetic acid and water.

For the preparation of cinnamic acid derivatives according to process 1, there can be used all processes which permit a splitting off of HA. If A is a hydroxyl group, then a dehydration can be carried out with conventional agents, for example glacial acetic acid, acetic anhydride, sulphuric acid, hydrogen sulphate, polyphosphoric acid, phosphorus oxychloride, thionyl chloride or phosphorus pentoxide, whereby it is preferable to work in an inert solvent, for example benzene, methylene chloride, carbon tetrachloride or the like. Dehydration with phosphorus pentoxide in boiling methylene chloride is preferred. The hydroxy compounds necessary for the dehydration can be prepared, for example, by a Raformatzky reaction from the corresponding aldehydes or ketones or they can be obtained by the reduction of the corresponding keto compounds either with a complex hydride, for example sodium borohydride, or by hydrogenation using Raney nickel as catalyst.

For splitting off a hydrogen halide (when A is a halogen atom), use can be made of basic agents, for example inorganic or organic bases, such as sodium hydroxide, potassium hydroxide, sodium acetate, sodium carbonate or potassium carbonate, as well as alcoholates, for example sodium methylate, or amines, for example triethylamine, dimethylaniline or pyridine. It is preferable to work in an inert solvent, for example dioxan, dimethyl sulphoxide, benzene, petroleum ether or an alcohol, such as ethanol or isopropanol.

The condensation of compounds of general formula (XV) with malonic acid derivatives takes place in known manner by the reaction of the two components in an appropriate solvent, for example pyridine, preferably in the presence of a primary or secondary amine, piperidine being preferred as secondary amine.

The reactions between compounds (XV) and phosphonic acid esters (PO-activated olefin formation according to Horner's method) is carried out in an inert solvent in the presence of a base. As inert solvent, there can be used, for example, diglyme, benzene, toluene, tetrahydrofuran, dimethylformamide and also ethers and petroleum ether. Examples of bases which can be used include sodamide, organo-lithium compounds, alcoholates (usually dissolved in the corresponding alcohol) and sodium hydride, as well as dimethyl sulphoxylate in dimethyl sulphoxide. The reaction is carried out either at ambient temperature or at an elevated temperature (boiling temperature of the solvent).

The protective groups for the piperazine to be temporarily introduced can, in principle, be any of the possible protective groups for secondary amines, acyl radicals and especially formyl, acetyl and benzoyl radicals being preferred. In the case of some reactions according to the above process, it has proved advantageous to use alkoxycarbonyl radicals and especially an ethoxycarbonyl radical. Insofar as no hydrogenolytic processes are included in the preparation process, as a preferred protective group, the benzyl radical is also to be mentioned.

The substituents Y in compounds of general formula (II) which can be converted into a —$COOR_2$ group include, for example, the nitrile, carbaldehyde, hydroxymethyl, aminomethyl and formyl groups.

A conversion of the substituents $R_2$ possibly to be carried out subsequently to the condensation according to processes (a) and (b) or subsequently to a chain change, can take place, for example, by saponification of carboxylic acid esters ($R_2$=alkyl) to the corresponding carboxylic acids ($R_2$=hydrogen) using mineral acids or alkali metal hydroxides in a polar solvent, such as water, methanol, ethanol, dioxan or acetone. The saponification is advantageously carried out with a strong base, such as sodium or potassium hydroxide, in a mixture of methanol and water at ambient temperature or at a moderately increased temperature. On the other hand, however, carboxylic acids can also be esterified in the usual way or esters with a particular residue $R_2$ can be converted into other esters with a different residue $R_2$ by transesterification. Esterification of the carboxylic acids is preferably carried out in the presence of an acid catalyst, for example hydrogen chloride, sulphuric acid, p-toluenesulphonic acid or of a strongly acidic ion exchange resin. Transesterifications, on the other hand, require the addition of a small amount of a basic substance, for example of an alkali metal or alkaline earth metal hydroxide or of an alkali metal alcoholate. For the esterification of the carboxyl group or for the transesterification, in principle use can be made of all alcohols. The lower monohydroxy alcohols are preferred, such as methanol, ethanol or propanol, as well as polyhydroxy alcohols, for example glycerol, or alcohols containing additional functional groups, such as ethanolamine or glycol ethers.

The amides according to the present invention derived from carboxylic acids of general formula (I) are preferably prepared by known methods from the carboxylic acids or reactive derivatives thereof, for example carboxylic acid halides, esters, azides, anhydrides or mixed anhydrides, by reaction with amines. The amine components can be, for example, ammonia, alkylamines and dialkylamines, as well as aminoalcohols, for example ethanolamine and 2-aminopropanol, and also amino acids, for example p-aminobenzoic acid, β-alanine and the like. Other valuable amine components include alkyl-, aralkyl- and arylpiperazines.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids can be reacted with the appropriate bases. Mixtures of carboxylic acids with appropriate alkali metal carbonates or hydrogen carbonates can also be used.

All the compounds of general formula (I), in which R is a hydrogen atom, can also be used as intermediates for the preparation of compounds of general formula (I) with the given meanings for R. The further working up to give the compounds according to the present invention can take place according to process (a) by acylation or alkylation.

Furthermore, all compounds of general formulae (XI) to (XVI) are new. Their further working up to give the compounds of general formula (I) according to the present invention takes place in the above-described way.

For the preparation of medicaments, the compounds of general formula (I) are mixed in known manner with appropriate pharmaceutical carrier substances, aroma, flavoring and coloring materials and formed, for example, into tablets or dragees or, with the addition of appropriate adjuvants, suspended or dissolved in water or an oil, for example olive oil.

The compounds of general formula (I) can be administered orally and parenterally in liquid or solid form. As injection medium, water is preferably used which contains the stabilizing agents, solubilising agents and/or buffers usual in the case of injection solutions. Additives of this kind include, for example, tartrate or borate buffers, ethanol, dimethyl sulphoxide, complex formers (such as ethylenediamine-tetraacetic acid), high molecular weight polymers (such as liquid polyethylene oxide) for viscosity regulation or polyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The dosage administered depends upon the age, the state of health and the weight of the recipient, the extent of the disease, the nature of possibly simultaneously carried out further treatments, the frequency of the treatment and the nature of the desired action. Usually, the daily dosage of the active compound is from 0.5 to 500 mg./kg. of body weight. Normally, 1.0 to 400 and preferably 2.0 to 200 mg./kg./day, in one or more administrations, are effective in order to obtain the desired results.

Preferred in the meaning of the present invention are, apart from the compounds of general formula (I) mentioned in the examples, as well as the esters and amides thereof, also the following:

1. 4-[4-(4-chlorocinnamyl)-piperazin-1-yl]-methylbenzoic acid
2. 4-{2-[4-(2-chlorobenzyl)-piperazin-1-yl]-ethyl}-benzoic acid and the n-butyl ester, 2-diethylaminoethyl ester and amide thereof
3. 4-{2-[4-(3-chlorobenzyl)-piperazin-1-yl]-ethyl}-benzoic acid and the diethylamide thereof
4. 4-{2-[4-(3-trifluoromethylbenzyl)-piperazin-1-yl]-ethyl}-benzoic acid
5. 4-{2-[4-(4-fluorobenzyl)-piperazin-1-yl]-ethyl}-benzoic acid
6. 4-{2-[4-(2-chlorocinnamyl)-piperazin-1-yl]-ethyl}-benzoic acid 7. 4-{2-[4-(3-bromocinnamyl)-piperazin-1-yl]-ethyl}-benzoic acid
8. 4-{2-[4-(4-nitrocinnamyl)-piperazin-1-yl]-ethyl}-benzoic acid
9. 4-{2-[4-(3-methoxycinnamyl)-piperazin-1-yl]-ethyl}-benzoic acid
10. 4-{2-[4-(4-cyanocinnamyl)-piperazin-1-yl]-ethyl}-benzoic acid
11. 4-{2-[4-(4-carboxycinnamyl)-piperazin-1-yl]-ethyl}-benzoic acid
12. 4-{2-[4-(3-trifluoromethylcinnamyl)-piperazin-1-yl]-ethyl}-benzoic acid
13. 4-{2-[4-(3-(4-chlorobenzyl)-propyl)-piperazin-1-yl]-ethyl}-benzoic acid
14. 4-{2-[4-(3-(4-cyanophenoxy)-propyl)-piperazin-1-yl]-ethyl}-benzoic acid
15. 4-{2-[4-(3-(4-acetaminophenoxy)-propyl)-piperazin-1-yl]-ethyl}-benzoic acid
16. 4-{2-[4-(3-(4carboxyphenoxy)-propyl)-piperazin-1-yl]-ethyl}-benzoic acid
17. 4-{2-[4-(3-trifluoromethylphenyl)-piperazin-1-yl]-ethyl}-benzoic acid
18. 4-{2-[4-(4-(4-chlorobenzoyl)-phenyl)-piperazin-1-yl]-ethyl}-benzoic acid
19. 4-{2-[4-(4-biphenylyl)-piperazin-1-yl]-ethyl}-benzoic acid
20. 4-{2-[4-(4-phenoxyphenyl)-piperazin-1-yl]-ethyl}-benzoic acid
21. 4-{2-[4-(4-benzyloxyphenyl)-piperazin-1-yl]-ethyl}-benzoic acid
22. 4-{2-[4-(2-benzylpropionyl)-piperazin-1-yl]-ethyl}-benzoic acid
23. 4-{2-[4-(2-chlorobenzoyl)-piperazin-1-yl]-propyl}-benzoic acid
24. 4-{2-[4-(4-chlorocinnamyl)-piperazin-1-yl]-propyl}-benzoic acid
25. 4-{1-[4-(4-chlorobenzoyl)-piperazin-1-yl]-prop-2-yl}-benzoic acid
26. 4-{1-[4-(4-chlorocinnamyl)-piperazin-1-yl]-prop-2-yl}-benzoic acid
27. 4-{3-[4-(4-chlorocinnamyl)-piperazin-1-yl]-propyl}-benzoic acid
28. 4-{4-(4-chlorocinnamyl)-piperazin-1-yl}-phenylacetic acid
29. 3-{4-[2-(4-(4-chlorobenzoyl)-piperazin-1-yl)-ethyl]-phenyl}-butyric acid
30. 4-{2-[4-(4-chlorobenzoyl)-piperazin-1-yl]-ethyl}-α-methylcinnamic acid
31. 4-{2-[4-(4-chlorocinnamyl)-piperazin-1-yl]-ethyl}-α-methylcinnamic acid
32. 4-{2-[4-(4-chlorobenzoyl)-piperazin-1-yl]-ethyl}-β-methylcinnamic acid
33. 4-{2-[4-(4-chlorocinnamyl)-piperazin-1-yl]-ethyl}-β-methylcinnamic acid.

The following examples are given for the purpose of illustrating the present invention:

EXAMPLE 1

Ethyl 4-(piperazin-1-yl)-benzoate

A mixture of 39.5 g. (0.24 mole) ethyl 4-aminobenzoate (free base), 140 ml. n-butanol and 47.1 g. (0.265 mole) bis-(2-chloroethyl)-amine hydrochloride is heated at reflux temperature for 36 hours, then 16.8 g. (0.12 mole) powdered anhydrous potassium carbonate are added thereto followed by further heating for 80 hours. The hot reaction mixture is then suction filtered, the filter cake is washed with some hot butanol and the combined filtrates are cooled. After standing overnight, the solid product obtained is filtered off with suction, washed twice with 50 ml. amounts of diethyl ether and dried. Yield: 33.4 g. (64% of theory) of yellow crystals which are recrystallised from ethanol/diethyl ether (2:1 v/v) to give 28.45 g. (55% of theory) of the desired product in the form of an almost colourless hydrochloride; m.p. 176°–178° C. The product is hydroscopic.

The free base (m.p. 76°–77° C.) is prepared by suspending 10 g. of the hydrochloride in 75 ml. diethyl ether, adding a concentrated aqueous ammonia solution dropwise thereto to give a strongly alkaline reaction, separating off the diethyl ether and extracting the aqueous phase twice with diethyl ether. After drying with anhydrous sodium sulphate, the ethereal solution is evaporated to give 8.4 g. (97% of theory) of the free base, which is not stable.

In an analogous way but using n-butyl 4-aminobenzoate, there is obtained n-butyl 4-(piperazin-1-yl)-benzoate in a yield of 43% of theory in the form of its hydrochloride; m.p. 178°–180° C. (recrystallised from isopropanol).

EXAMPLE 2

4-(1-n-Hexadecylpiperazin-4-yl)-benzoic acid (a) A mixture of 300 ml. butane-2-one, 27.0 g. (0.1 mole) ethyl 4-(piperazin-1-yl)-benzoate hydrochloride, 28 g. powdered anhydrous potassium carbonate and 30.5 g. (0.1 mole) 1-bromohexadecane is maintained at reflux temperature for 30 hours. The reaction mixture is then suction filtered while still hot, the filter cake is washed with hot butan-2-one and the combined filtrates are evaporated. Beige-coloured crystals remain behind; m.p. 76°–78° C. These crystals are dissolved in a little diethyl ether, mixed with a sufficient amount of hydrogen chloride-containing diethyl ether and the hydrochloride formed is separated by suction filtration to give 47.7 g. of crude product (96% of theory) which is recrystallised from 150 ml. ethanol and 50 ml. diethyl ether to give 29.4 g. of sand-coloured ethyl 4-(1-n-hexadecylpiperazin-4-yl)-benzoate hydrochloride; m.p. 193°–196° C.

(b) A mixture of 29.4 g. (59.4 mmole) of the above ethyl ester, 148.5 ml. 1N potassium hydroxide solution and 148.5 ml. ethanol is maintained at reflux temperature for 8 hours, then cooled and the precipitate formed is filtered off with suction, dissolved in boiling water and 150 ml. 1N hydrochloric acid added thereto. After cooling, the product obtained is filtered off with suction, washed with water and dried at 50° C. to give 21.7 g. (78% of theory) 4-(1-n-hexadecylpiperazin-4-yl)-benzoic acid hydrochloride; m.p. 252°–254° C.

Analogously to Example 2(a), from ethyl 4-(piperazin-1-yl)-benzoate there are prepared the following compounds:

(a1) with benzyl chloride:
ethyl 4-[1-(4-chlorobenzyl)-piperazin-1-yl]-benzoate. Yield 73% of hydrochloride; m.p. 172°–173° C. (recrystallised from ethanol and diethyl ether (5:1 v/v)).

(a2) with 1-bromo-2-phenoxyethane:
ethyl 4-[1-(2-phenoxyethyl)-piperazin-4-yl]-benzoate. Yield: 68% of theory of hydrochloride; m.p. 200°–202° C. (recrystallised from ethanol and diethyl ether (1:3 v/v)).

(a3) with 1-bromo-3-phenylpropane:

ethyl 4-[1-(3-phenylpropyl)-piperazin-4-yl]-benzoate.
Yield: 58% of theory; m.p. 175°–178° C. (recrystallised from ethanol and ligroin).

Analogously to Example 2(b), from the corresponding ethyl benzoates there are prepared the following acids:

(b1) 4-[1-(4-chlorobenzyl)-piperazin-4-yl]-benzoic acid.
  Yield 75% of theory of hydrochloride; m.p. 282°–284° C.
(b2) 4-[1-(2-phenoxyethyl)-piperazin-4-yl]-benzoic acid.
  Yield 92% of theory of hydrochloride; m.p. 240°–242° C.
  (recrystallised from aqueous acetone).

EXAMPLE 3

Ethyl 4-[1-(4-chlorophenacyl)-piperazin-4-yl]-benzoate

A mixture of 11.7 g. (50 mmole) ethyl 4-(piperazin-1-yl)-benzoate, 13.8 g. (0.1 mole) powdered anhydrous potassium carbonate, 125 ml. acetonitrile and 11.7 g. (50 mmole) 2-bromo-4′-chloroacetophenone (p-chlorophenacyl bromide) is stirred for 20 hours at 20° C. The reaction mixture is then suction filtered and the filter cake is washed with acetone. The combined organic phases are evaporated to dryness in a vacuum to give 15.4 g. (80% of theory) of crude product. After recrystallisation from ethyl acetate, there are obtained 9.8 g. (51% of theory) of pure product; m.p. 152°–153° C. and from the mother liquor a further 1.4 g. (7% of theory) (m.p. 150°–152° C.) of product are obtained.

This ester can be hydrolysed to the acid without decomposition.

Analogously thereto, from n-butyl 4-(piperazin-1-yl)-benzoate there are prepared the following compounds:
(3a) with 4-methoxybenzyl chloride:
  n-butyl 4-[1-(4-methoxybenzyl)-piperazin-4-yl]-benzoate.
  Yield 72% of theory; m.p. 77°–78° C. (recrystallised from acetonitrile)
(3b) with phenethyl bromide:
  n-butyl 4-[1-(phenethyl)-piperazin-4-yl]-benzoate.
  Yield 74% of theory; m.p. 67°–68° C. (recrystallised from acetonitrile)

EXAMPLE 4

Ethyl 4-{1-[2-(3,5-di-tert.-butyl-4-hydroxyphenyl)-ethyl]-piperazin-4-yl}-benzoate To a mixture of 30.0 g. (0.12 mole) 3,5-di-tert.-butyl-4-hydroxyphenethyl alcohol and 40 ml. anhydrous pyridine, are added portionwise at 0°–5° C., in the course of one hour, 25.4 g. (132 mmole) tosyl chloride. Subsequently, the reaction mixture is stirred for 4 hours at 0° C., then poured on to about 500 ml. ice water and extracted with diethyl ether. The ether phase is washed twice with water, dried with anhydrous sodium sulphate and evaporated in a vacuum (bath temperature maximum 20° C., otherwise decomposition occurs). The residue is then recrystallised from ligroin to give 39.5 g. (82% of theory) p-toluenesulphonic acid (3,5-di-tert.-butyl-4-hydroxyphenethyl ester); m.p. 104°–105° C.

A mixture of 20.2 g. (50 mmole) p-toluenesulphonic acid (3,5-di-tert.-butyl-4-hydroxyphenethyl ester), 11.7 g. (50 mmole) ethyl 4-(piperazin-1-yl)-benzoate, 6.9 g. (50 mmole) powdered anhydrous potassium carbonate and 200 ml. butan-2-one is maintained at reflux temperature for 18 hours. The reaction mixture is then suction filtered, the filter cake is washed with acetone and the filtrate is evaporated in a vacuum. The residue is recrystallised from ligroin to give 15.7 g. (68% of theory) ethyl 4-{1-[2-(3,5-di-tert.-butyl-4-hydroxyphenyl)-ethyl]-piperazin-4-yl}-benzoate; m.p. 131°–132° C.

EXAMPLE 5

Ethyl 4-[1-(2-phenoxypropyl)-piperazin-4-yl]-benzoate

In 60 ml. HMPT there are dissolved 17.6 g. (75 mmole) ethyl 4-(piperazin-1-yl)-benzoate and 17.28 g. (75 mmole) p-toluenesulphonic acid (2-phenoxypropyl ester) and the solution is flushed with nitrogen and kept for 12 hours at reflux temperature under nitrogen. Thereafter, a further 10 mmole of tosylate are added. The reaction mixture is maintained at reflux temperature for a further 20 hours, another 1.7 g. tosylate is added thereto and heating continued for 6 hours. The reaction mixture is then cooled, stirred into water and extracted three times with methylene chloride. The combined organic phases are washed with water, dried with anhydrous magnesium sulphate and mixed with hydrogen chloride-containing ether. After evaporation, the residue crystallises to give 11.4 g. (34% of theory) of product which, after recrystallisation from ethanol/diethyl ether (1:3 v/v) gives 8.1 g. (24% of theory) ethyl 4-[1-(2-phenoxypropyl)-piperazin-4-yl]-benzoate hydrochloride; m.p. 200°–202° C.

Instead of the tosylate, halides can here also be used:

n-butyl 4-[1-(4-chlorocinnamyl)-piperazin-4-yl]-benzoate

A mixture of 9.4 g. (50 mmole) 4-chlorocinnamyl chloride and 13.1 g. (50 mmole) n-butyl 4-(piperazin-1-yl)-benzoate in 40 ml. hexamethylphosphoric acid triamide is heated for 10 hours to 60° C., 6.9 g. (50 mmole) potassium carbonate are added thereto and stirring continued for 5 hours at 60° C. After cooling, the reaction mixture is diluted with the tenfold amount of water, the organic components are taken up in ethyl acetate and the dried ethyl acetate solution is evaporated. The residue is recrystallised from methanol to give 10.0 g. (48%) of desired product; m.p. 115°–117° C. The hydrochloride melts at 166°–168° C.

EXAMPLE 6

Ethyl 4-[1-(4-chlorobenzoyl)-piperazin-4-yl]-benzoate

To a mixture of 13.5 g. (50 mmole) ethyl 4-(piperazin-1-yl)-benzoate hydrochloride and 130 ml. anhydrous pyridine are added, at 5°–10° C., 50 mmole 4-chlorobenzoyl chloride. The temperature is allowed to come to 20° C. and the reaction mixture is subsequently stirred for 6 hours at 40° C. After cooling, it is stirred into 400 ml. ice water, extracted twice with 250 ml. amounts of methylene chloride and the organic phase is dried with anhydrous sodium sulphate and evaporated in a vacuum. The residue is triturated with ligroin and recrystallised from 150 ml. ethanol to give 15.6 g. of the desired product as colourless crystals; m.p. 147°–150° C.

Analogously thereto, from ethyl 4-(piperazin-1-yl)-benzoate hydrochloride there is prepared, by reaction with 4-chlorocinnamoyl chloride, ethyl 4-[1-(4-chlorocinnamoyl)-piperazin-4-yl]-benzoate. Yield 82% of theory; m.p. 148°–150° C. (recrystallised from ethanol).

EXAMPLE 7

Ethyl 4-{1-[3-(3,5-di-tert.-butyl-4-hydroxyphenyl)-propionyl]-piperazin-4-yl}-benzoate A mixture of 23.4 g. (0.1 mole) ethyl 4-(piperazin-1-yl)-benzoate (base), 600 ml. xylene and 27.8 g. (0.1 mole) 3-(3,5-di-tert.-butyl-4-hydroxyphenyl)-propionic acid is boiled under a water separator for 28 hours, then evaporated to dryness in a vacuum and the residue is taken up with diethyl ether. For the removal of unreacted ethyl 4-(piperazin-1-yl)-benzoate, the ether solution is extracted with 1N hydrochloric acid, washed with water and aqueous sodium bicarbonate solution, dried with anhydrous sodium sulphate and mixed with hydrogen chloride-containing diethyl ether, whereby the hydrochloride precipitates out. This is washed with diethyl ether and recrystallised from ethanol to give 32.0 g. (60% of theory) of the desired product as colourless crystals; m.p. 196°-198° C.

In an analogous manner, from n-butyl 4-(piperazin-1-yl)-benzoate and 4-chlorophenylacetic acid there is obtained n-butyl 4-[1-(4-chlorophenacetyl)-piperazin-4-yl]-benzoate:

A mixture of 17.0 g. (0.1 mole) p-chlorophenylacetic acid, 26.2 g. (0.1 mole) n-butyl 4-(piperazin-1-yl)-benzoate (base) and 1 liter xylene is heated for 70 hours, while stirring, under a water separator. The reaction mixture is then evaporated and the residue, which gradually crystallises after standing for several days, is recrystallised from ethanol to give 17.2 g. (42%) of the desired product; m.p. 85°-86° C.

EXAMPLE 8 n-Butyl 4-(1-methanesulphonylpiperazin-4-yl)-benzoate

To a mixture of 27 g. (0.1 mole) n-butyl 4-(piperazin-1-yl)-benzoate hydrochloride and 270 ml. anhydrous pyridine are added at 5°-10° C. 11.4 g. (0.1 mole) methanesulphonyl chloride. The reaction mixture is left to stand overnight at 20° C. and then poured into 250 ml. ice water and extracted twice with methylene chloride. The extracts are dried with anhydrous sodium sulphate and evaporated in a vacuum. After trituration of the residue with ligroin, 17.1 g. (55% of theory) of the desired product are obtained as yellow crystals; m.p. 145°-150° C.

Analogously thereto, from ethyl 4-(piperazin-1-yl)-benzoate hydrochloride there are obtained the following products:

(8a) with 4-chlorobenzenesulphochloride:
   ethyl 4-[1-(4-chlorobenzenesulphonyl)-piperazin-4-yl]-benzoate
   Yield 65% of theory; m.p. 158°-159° C. (recrystallised from ethyl acetate and ligroin)
(8b) with benzenesulphochloride:
   ethyl 4-(1-benzenesulphonylpiperazin-4-yl)-benzoate
   Yield 95% of theory; m.p. 102°-104° C.
(8c) with p-toluenesulphochloride:
   ethyl 4-[1-(4-methylbenzenesulphonyl)-piperazin-4-yl]-benzoate
   Yield 84% of theory; m.p. 122°-124° C. (recrystallised from ethanol and ligroin).

EXAMPLE 9 n-Butyl 4-(1-Methylpiperazin-4-yl)-benzoate 19.6 g. (75 mmole) n-Butyl 4-(piperazin-1-yl)-benzoate are heated to reflux temperature for 12 hours in a mixture of 112 ml. 80% formic acid and 37.5 ml. 40% formaldehyde solution. After cooling, the reaction mixture is poured into 2.5 liters of water, rendered alkaline with 10N aqueous sodium hydroxide solution and extracted with methylene chloride. The methylene chloride extracts are dried and evaporated to give 17.8 g. (86% of theory) of the desired product; m.p. 118°-120° C.

EXAMPLE 10

3-[1-(4-Butoxycarbonylphenyl)-piperazin-4-yl]-propanesulphonic acid

A solution of 6.1 g. (50 mmole) γ-propanesultone, 13.1 g. (50 mmole) butyl 4-piperazin-1-yl)-benzoate and 75 ml. ethanol is stirred for 8 days at 20° C. The precipitate obtained is then filtered off with suction and washed with ethanol to give 17.3 g. (90% of theory) of the desired product; m.p. 232°-234° C. (recrystallised from aqueous ethanol).

EXAMPLE 11 n-Butyl 4-{1-[4-(2-hydroxypropyl)-phenyl]-piperazin-4-yl}-benzoate

A mixture of 13.1 g. (50 mmole) n-butyl 4-(piperazin-1-yl)-benzoate, 2.9 g. (50 mmole) propylene oxide and 6 ml. methanol is stirred for 24 hours at 20° C. The solvent is then evaporated off and the residue is triturated with ligroin to give a yield of 78% of theory of the desired product; m.p. 85°-86° C.

EXAMPLE 12

Ethyl 4-[1-(3,5-di-tert.-butyl-4-hydroxycinnamoyl)-piperazin-4-yl]-benzoate

To a solution of 18.75 g. (80 mmole) ethyl 4-(piperazin-1-yl)-benzoate and 22.1 g. (80 mmole) 3,5-di-tert.-butyl-4-hydroxycinnamic acid in 160 ml. anhydrous pyridine is added dropwise, with ice cooling, a solution of 5.5 g. (40 mmole) phosphorus trichloride and 25 ml. anhydrous pyridine and the reaction mixture is further stirred for 1 hour with ice cooling, then poured on to ice and acidified with concentrated hydrochloric acid. The aqueous phase is extracted with ethyl acetate and the extracts are washed three times with 0.5N hydrochloric acid, dried and evaporated. The residue is recrystallised twice from a mixture of 240 ml. ethanol and 80 ml. water to give 29.2 g. (74%) of the desired product; m.p. 147°-150° C.

EXAMPLE 13

4-[1-(2-Phenoxypropyl)-piperazin-4-yl]-benzoic acid

A mixture of 20.2 g. (50 mmole) ethyl 4-[1-(2-phenoxypropyl)-piperazin-4-yl]-benzoate hydrochloride, 150 ml. 1N potassium hydroxide solution and 150 ml. ethanol is stirred for 2.5 hours at 80° C. The ethanol is subsequently distilled off in a vacuum and the aqueous phase is adjusted to pH 5.5 with dilute hydrochloric acid. The precipitated crystals are filtered off with suction and recrystallised from ethyl acetate to give 8.6 g. (50.5% of theory) 4-[1-(2-phenoxypropyl)-piperazin-4-yl]-benzoic acid; m.p. 152°-154° C.

In some cases, it is only possible with difficulty to precipitate out the free acid by adjustment of the isoelectric point. In such cases, acidification with hydrochloric acid is carried out to precipitate out the hydrochloride.

Analogously to the above example, there are prepared the following compounds:

(13a) 4-[1-(4-chlorocinnamoyl)-piperazin-4-yl]-benzoic acid
Yield 90% of theory; m.p. above 286° C. (decomp.)

(13b) 4-{1-[3-(3,5-di-tert.-butyl-4-hydroxyphenyl)-propionyl]-piperazin-4-yl}-benzoic acid
Yield 65% of theory; m.p. 235°–238° C. (recrystallised from ethyl acetate and ligroin 1:1 v/v)

(13c) 4-(1-methanesulphonylpiperazin-4-yl)-benzoic acid
Yield 84% of theory; m.p. >300° C.

(13d) 4-[1-(4-chlorobenzenesulphonyl)-piperazin-4-yl]-benzoic acid
Yield 95% of theory; m.p. 289°–291° C.

(13e) 4-[1-(4-methoxybenzyl)-piperazin-4-yl]-benzoic acid
Yield 79% of theory of hydrochloride; m.p. 272°–273° C.

(13f) 4-(1-phenethyl-piperazin-4-yl)-benzoic acid
Yield 93% of theory of hydrochloride; m.p. 292°–293° C.

(13g) 4-[1-(4-chlorocinnamyl)-piperazin-4-yl]-benzoic acid
Yield 73% of theory; m.p. 231°–233° C. (recrystallised from ethanol). The hydrochloride melts at 261°–264° C.
(recrystallised from aqueous ethanol).

(13h) 4-[1-(4-chlorophenacetyl)-piperazin-4-yl]-benzoic acid
Yield 70% of theory; m.p. 250°–252° C.

(13i) 4-[1-(3-phenylpropyl)-piperazin-4-yl]-benzoic acid
Yield 77% of theory of hydrochloride monohydrate; m.p. 281°–284° C.

(13j) 4-(1-methylpiperazin-4-yl)-benzoic acid
Yield 71% of theory; m.p. 288°–292° C.

(13k) 3-[1-(4-hydroxycarbonylphenyl)-piperazin-4-yl]-propanesulphonic acid
Yield 91% of theory; m.p. >340° C.

(13l) 4-{1-[4-(2-hydroxypropyl)-phenyl]-piperazin-4-yl}-benzoic acid
Yield 84% of theory of dihydrochloride monohydrate;
m.p. 276°–278° C.

(13m) 4-[1-(3,5-di-tert.-butyl-4-hydroxycinnamoyl)-piperazin-4-yl]-benzoic acid
Yield 70% of theory; m.p. 272° C. (recrystallised from ethanol)

(13n) 4-(1-benzenesulphonylpiperazin-4-yl)-benzoic acid
Yield 81% of theory; m.p. 292°–295° C.

(13o) 4-[1-(p-toluenesulphonyl)-piperazin-4-yl]-benzoic acid
Yield 94% of theory; m.p. 297°–300° C.

EXAMPLE 14.

Methyl 4-(piperazin-1-ylmethyl)-benzoate

A mixtue of 38 g. (0.2 mole) piperazine hexahydrate, 28 g. (0.2 mole) piperazine dihydrochloride and 150 ml. methanol is mixed, while stirring at ambient temperature, with 45 g. (0.2 mole) methyl 4-bromomethylbenzoate. The reaction mixture is left to stand for 2 days and suction filtered from the precipitate. The clear solution is evaporated and the residue is recrystallised from ethanol to give 39 g. (64%) of the desired compound as a monohydrochloride; m.p. 226°–227° C.

The desired compound can also be prepared in the following way:

(a) A mixture of 7.9 g. (50 mmole) 1-ethoxycarbonyl-piperazine, 150 ml. butan-2-one, 6.9 g. (0.1 mole) powdered potassium carbonate and 12.0 g. (52.5 mmole) methyl 4-(bromoethyl)-benzoate is maintained at reflux temperature for 3 days. It is then suction filtered and the filter cake washed with acetone. The combined filtrates are evaporated in a vacuum, the residue is taken up in diethyl ether, the ether phase is washed with water and dried with anhydrous sodium sulphate. The hydrochloride is precipitated out by the addition of hydrogen chloride-containing diethyl ether. After recrystallisation from dioxan there are obtained 15.5 g. (86% of theory) methyl 4-[1-(ethoxycarbonyl)-piperazin-4-ylmethyl]-benzoate hydrochloride; m.p. 201°–202° C.

(b) A mixture of 10.2 g. (33 mole) methyl 4-[1-(ethoxycarbonyl)-piperazin-4-yl]-benzoate hydrochloride and 100 ml. concentrated hydrochloric acid is kept at 95° C. for 60 hours, then cooled strongly, mixed with acetone and the precipitate obtained filtered off with suction to give 8.0 g. (83% of theory) 4-(piperazin-1-ylmethyl)-benzoic acid dihydrochloride; m.p. from 270° C. (decomp.).

(c) A mixture of 43.7 g. (0.15 mole) 4-piperazin-1-ylmethyl)-benzoic acid dihydrochloride and 300 ml. anhydrous methanol is gassed with hydrogen chloride up to saturation, the temperature being allowed to increase to about 55° C. Subsequently, the reaction mixture is maintained for 1 hour at 55° C. and allowed to react to completion overnight at 20° C. After concentration to half the volume, it is strongly cooled, suction filtered and the product dried to give 42.1 g. (91% of theory) methyl 4-(piperazin-1-ylmethyl)-benzoate dihydrochloride; m.p. 252°–253° C.

EXAMPLE 15

Methyl 4-[1-(benzenesulphonyl)-piperazin-4-ylmethyl]-benzoate

A mixture of 11.5 g. (50 mmole) methyl 4-bromomethylbenzoate, 11.3 g. (50 mmole) 1-benzenesulphonyl-piperazine, 6.91 g. (50 mmole) powdered potassium carbonate and 100 ml. butan-2-one is maintained at reflux temperature for 20 hours, then suction filtered while hot and the filtrate evaporated. After cooling, the product is filtered off with suction and recrystallised from methanol to give 11.6 g. (62% of theory) of the desired product; m.p. 145°–146° C.

In an analogous manner, from methyl 4-bromomethylbenzoate, there are prepared the following compounds:

(15a) with 1-(2-phenoxypropyl)-piperazine:
methyl 4-[1-(2-phenoxypropyl)-piperazin-4-ylmethyl]-benzoate
Yield 65% of theory of hydrochloride; m.p. 242°–244° C.

(15b) with 1-(4-chlorobenzyl)-piperazine:
methyl 4-[1-(4-chlorobenzyl)-piperazin-4-ylmethyl]-benzoate
Yield 76% of theory; m.p. 98°–99° C. (recrystallised from methanol)

(15c) with 1-(n-hexadecyl)-piperazine:
methyl 4-[1-(n-hexadecyl)-piperazin-4-ylmethyl]-benzoate Yield 72% of theory; m.p. 47°–48° C. (recrystallised from methanol)

(15d) with 1-(4-chlorophenyl)-piperazine:
methyl 4-[1-(4-chlorophenyl)-piperazin-4-ylmethyl]-benzoate
Yield 91% of theory of hydrochloride; m.p. 208° C. The free base melts at 109° C. (recrystallised from isopropanol)

(15e) with 1-(3,5-di-tert.-butyl-4-hydroxyphenethyl)-piperazine:
methyl 4-[1-(3,5-di-tert.-butyl-4-hydroxyphenethyl)-piperazin-4-ylmethyl]-benzoate
Yield 61% of theory; m.p. 103°–104° C. (recrystallised from isopropanol).

EXAMPLE 16

Methyl 4-[1-(2-hydroxypropyl)-piperazin-4-ylmethyl]-benzoate

This is prepared analogously to Example 11 from methyl 4-(piperazin-1-ylmethyl)-benzoate and propylene oxide. Yield 63% of theory; m.p. 63°–64° C.

EXAMPLE 17

Methyl 4-[1-(4-chlorobenzoyl)-piperazin-4-ylmethyl]-benzoate

To a solution of 15.3 g. (50 mmole) methyl 4-(piperazin-1-ylmethyl)-benzoate and 175 ml. anhydrous pyridine, there is added dropwise, at 0°–5° C., 8.7 g. (50 mmole) 4-chlorobenzoyl chloride and the reaction mixture kept for a further hour at 0° to 5° C., then overnight at 20° C. The reaction mixture is stirred into ice water and the precipitated product is filtered off with suction, washed with water and dried to give 18.5 g. (quantitative) of the desired product; m.p. 134°–135° C.

In analogous manner, from methyl 4-(piperazin-1-ylmethyl)-benzoate there is obtained, by reaction with 4-chlorocinnamoyl chloride, methyl 4-[1-(4-chlorocinnamoyl)-piperazin-4-ylmethyl]-benzoate. Yield: 84% of theory; m.p. 137°–138° C. (recrystallised from methanol).

EXAMPLE 18

4-[1-(n-Hexadecyl)-piperazin-4-ylmethyl]-benzoic acid

A mixture of 40 mmole methyl 4-[1-(n-hexadecyl)-piperazin-4-ylmethyl]-benzoate, 100 ml. 6N hydrochloric acid and 20 ml. dioxan is maintained at reflux temperature for 16 hours, then concentrated, cooled and suction filtered. After recrystallisation from a DMF-water mixture, there is obtained a yield of 62% of theory of the desired product as a hydrochloride; m.p. 245° C.

EXAMPLE 19

A mixture of the ethyl ester of an appropriate acid, 1N aqueous potassium hydroxide solution (threefold molar amount) and an equal volume of methanol is heated to 40° to 60° C. until starting material can no longer be detected in the thin layer chromatogram. The methanol is then distilled off and the residue is neutralized with an amount of 1N hydrochloric acid equivalent to the amount of aqueous potassium hydroxide solution used. The free piperazinecarboxylic acid is now filtered off with suction or, if it does not precipitate out, is precipitated as the hydrochloride by acidification with hydrochloric acid. The product is filtered off with suction, dried and recrystallised.

The following acids are prepared according to this process:

(19a) 4-[1-(2-hydroxypropyl)-piperazine-4-ylmethyl]-benzoic acid
Yield 69% of theory of dihydrochloride; m.p. 281°–283° C.

(19b) 4-[1-(3,5-di-tert.-butyl-4-hydroxyphenethyl)-piperazin-4-ylmethyl]-benzoic acid
Yield 76% of theory of dihydrochloride; m.p. 285°–288° C. (decomp.)

(19c) 4-[1-(4-chlorophenyl)-piperazin-4-ylmethyl]-benzoic acid
Yield 60% of theory of hydrochloride; m.p. 258°–261° C.
(recrystallised from water)

(19d) 4-[1-(4-chlorobenzoyl)-piperazin-4-ylmethyl]-benzoic acid
Yield 69% of theory of hydrochloride; m.p. 270°–273° C.

(19e) 4-[1-(4-chlorocinnamoyl)-piperazin-4-ylmethyl]-benzoic acid
Yield 92% of theory of hydrochloride; m.p. 289°–290° C.

(19f) 4-[1-(benzenesulphonyl)-piperazin-4-ylmethyl]-benzoic acid
Yield 72% of theory of hydrochloride; m.p. 268°–269° C.
(recrystallised from aqueous ethanol)

EXAMPLE 20

(1) Ethyl 4-[2-(piperazin-1-yl)-ethyl]-benzoate (a) A mixture of 51.4 g. (0.2 mole) ethyl 4-(2-bromoethyl)-benzoate, 500 ml. butan-2-one, 35.2 g. (0.2 mole) benzylpiperazine and 55.3 g (0.4 mole) powdered anhydrous potassium carbonate is maintained at reflux temperature for 48 hours, then filtered with suction and the filtrate evaporated in a vacuum. The residue is dissolved in ether. The ether phase is washed several times with water, dried with anhydrous sodium sulphate and then mixed with hydrogen chloride-containing diethyl ether in sufficient amount. After suction filtration and drying, there are obtained 15.9 g. (75% of theory) ethyl 4-[2-(1-benzylpiperazin-4-yl)-ethyl]-benzoate dihydrochloride; m.p. 277°–278° C. (decomp.).

(b) A mixture of 63.8 g. (0.15 mole) ethyl 4-[2-(1-benzylpiperazin-4-yl)-ethyl]-benzoate dihydrochloride, 350 ml. water, 650 ml. ethanol and about 5 g. 10% palladium charcoal is hydrogenated at 20° C. and atmospheric pressure. Subsequently, the alcohol is distilled in a vacuum, the cooled solution is rendered distinctly alkaline with semiconcentrated aqueous ammonia and immediately extracted several times with diethyl ether. The combined ether extracts are dried with anhydrous potassium carbonate, then sufficient hydrogen chloride-containing diethyl ether is added thereto and the product is filtered off with suction and dried to give 38.5 g. (77% of theory) of the desired product as a dihydrochloride; m.p. 276° C. (decomp.) (recrystallised from aqueous ethanol).

(2) Ethyl 4-[3-(piperazin-1-yl)-propyl]-benzoate is prepared in an analogous manner:

(a₁) from 1-benzylpiperazine and ethyl 4-(3-bromopropyl)-benzoate there is prepared ethyl 4-[3-(1-benzylpiperazin-4-yl)-propyl]-benzoate dihydrochloride in a yield of 76% of theory; m.p. 253°–254° C. (recrystallised from ethanol).

(a₂) Hydrogenation of the benzyl compound in a mixture of ethanol and 2N hydrochloric acid (4:1 v/v) in the presence of 10% palladium-charcoal gives ethyl 4-[3-(piperazin-1-yl)-propyl]-benzoate dihydrochloride in a yield of 93% of theory; m.p. 228°–230° C. (recrystallised from ethanol).

EXAMPLE 21

Ethyl 4-{2-[1-(4-methoxybenzyl)-piperazin-4-yl]-ethyl}-benzoate

A mixture of 250 ml. butan-2-one, 15.47 g. (75 mmole) 1-(4-methoxybenzyl)-piperazine, 19.3 g. (75 mmole) ethyl 4-(2-bromoethyl)-benzoate and 20.7 g. (0.15 mole) powdered potassium carbonate is maintained at reflux temperature for 60 hours, then suction filtered while hot and the filtrate evaporated in a vacuum. After the addition of diethyl ether, the product crystallises, the yield being 17.5 g. (61% of theory) of the desired product; m.p. 75°–76° C. The hydrochloride is precipitated from the filtrate by means of hydrogen chloride-containing diethyl ether. After recrystallisation from aqueous ethanol, there are obtained 7.6 g. (23% of theory) of the desired product; m.p. 280°–281° C.

In analogous manner, from ethyl 4-(2-bromoethyl)-benzoate there are prepared the following compounds:

(21a) with 1-methylpiperazine: methyl 4-[2-(1-methylpiperazin-4-yl)-ethyl]-benzoate Yield 66% of theory of hydrochloride; m.p. 273° C. (recrystallised from ethanol)

(21b) with 1-(2-hydroxypropyl)-piperazine:

ethyl 4-{2-[1-(2-hydroxypropyl)-piperazin-4-yl]-ethyl}-benzoate

Yield 75% of theory of hydrochloride; m.p. 271°–272° C.

(recrystallised from ethanol). Free base: m.p. 128°–129° C.

(21c) with 1-[1-(3,5-di-tert.-butyl-4-hydroxybenzoyl)-ethyl]-piperazine in acetonitrile:

ethyl 4-{2-[1-(1-(3,5-di-tert.-butyl-4-hydroxybenzoyl)-ethyl)-piperazin-4-yl]-ethyl}-benzoate Yield 70% of theory of dihydrochloride; m.p. 236°–240° C.

(21d) with 1-(phenethyl)-piperazine:

ethyl 4-{2-[1-(phenethyl)-piperazin-4-yl]-ethyl}-benzoate

Yield 67% of theory of dihydrochloride; m.p. 289° C. (decomp.)

(21e) with 1-(4-chlorophenyl)-piperazine:

ethyl 4-{2-[1-(4-chlorophenyl)-piperazin-4-yl]-ethyl}-benzoate

Yield 56% of theory of hydrochloride; m.p. 210° C. (recrystallised from aqueous ethanol) (21f) with 1-[2-(4-tolyloxy)-propyl]-piperazine:

ethyl 4-{2-[1-(2-(4-methylphenoxy)-propyl)-piperazin-4-yl]-ethyl}-benzoate

Yield 69% of theory of dihydrochloride; m.p. 247°–248° C.

(21g) with 1-(4-phenoxyphenyl)-piperazine:

ethyl 4-{2-[1-(4-phenoxyphenyl)-piperazin-4-yl]-ethyl}-benzoate

Yield 78% of theory of dihydrochloride; m.p. 193°–194° C.

(recrystallised from ethanol). The free base melts at 96°–97° C. (recrystallised from diethyl ether)

(21h) with 1-(4-benzyloxyphenyl)-piperazine:

ethyl 4-{2-[1-(4-benzyloxyphenyl)-piperazin-4-yl]ethyl}-benzoate

Yield 55% of theory; m.p. 145°–146° C. (recrystallised from ethyl acetate/diethyl ether)

(21i) with 1-(3-trifluoromethylphenyl)-piperazine:

ethyl 4-{2-[1-(3-trifluoromethylphenyl)-piperazin-4-yl]-ethyl}-benzoate

Yield 49% of theory of hydrochloride; m.p. 183°–185° C.

(recrystallised from ethanol)

In an analogous manner, from methyl 4-(2-bromoethyl)-benzoate there are obtained:

(21j) with 1-(2-chlorobenzyl)-piperazine:

methyl 4-{2-[1-(2-chlorobenzyl)-piperazin-4-yl]-ethyl}-benzoate

Yield 60% of theory of dihydrochloride; m.p. 228°–230° C. The free base melts at 68°–70° C. (recrystallised from ligroin)

(21k) with 1-(3,5-di-tert.-butyl-4-hydroxyphenenthyl)-piperazine:

methyl 4-{2-[1-(3,5-di-tert.-butyl-4-hydroxyphenethyl)-piperazin-4-yl]-ethyl}-benzoate Yield 76% of theory; m.p. 109°–110° C. Dihydrochloride m.p. 274° C. (recrystallised from ethanol)

In an analogous manner, from n-butyl 4-(2-bromoethyl)-benzoate there is obtained:

(21l) with 1-(2-chlorobenzyl)-piperazine:

n-butyl 4-{2-[1-(2-chlorobenzyl)-piperazin-4-yl]-ethyl}-benzoate

Yield 53% of theory of dihydrochloride; m.p. 228°–230° C.

(recrystallised from n-butanol)

EXAMPLE 22

Ethyl 4-{2-[1-(2-phenoxypropyl)-piperazin-4-yl]-ethyl}-benzoate

A mixture of 8.2 g. (37 mmole) 1-(2-phenoxypropyl)-piperazine, 9.57 g. (37 mmole) ethyl 4-(2-bromoethyl)-benzoate, 3.77 g. (37 mmole) triethylamine and 100 ml. anhydrous tetrahydrofuran is heated for 36 hours at reflux temperature and then evaporated. The residue is taken up in diethyl ether and the hydrochloride precipitated from this solution with hydrogen chloride-containing diethyl ether to give 14.7 g. (84% of theory) of the desired compound as a hydrochloride; m.p. 232° C.

The following compounds are prepared in an analogous manner, using ethyl 4-(2-bromoethyl)-benzoate:

(22a) with 1-(2-methyl-3-phenylpropyl)-piperazine dihydrochloride:

ethyl 4-{2-[1-(2-methyl-3-phenylpropyl)-piperazin-4-yl]-ethyl}-benzoate

Yield 53% of theory of dihydrochloride; m.p. 262° C.

(22b) with 1-[3-(4-chlorophenyl)-2-methylpropyl]-piperazine dihydrochloride:

ethyl 4-{2-[1-(3-(4-chlorophenyl)-2-methylpropyl)-piperazin-4-yl]-ethyl}-benzoate Yield 56% of theory of dihydrochloride; m.p. 278°–279° C. (recrystallised from ethanol).

EXAMPLE 23

Ethyl 4-{2-[1-(4-chlorocinnamyl)-piperazin-4-yl]-ethyl}-benzoate

A mixture of 150 ml. butan-2-one, 9.45 g. (36 mmole) ethyl 4-[2-(piperazin-1-yl)-ethyl]-benzoate, 7.5 g. (40 mmole) 4-chlorocinnamyl chloride and 5.55 g. (40 mmole) pulverised anhydrous potassium carbonate is maintained at reflux temperature for 40 hours, then suction filtered while hot and evaporated. The crude product is dissolved in ethyl acetate. By the addition of hydrogen chloride-containing diethyl ether, the dihydrochloride is precipitated. The yield is 78% of theory; m.p. 282° C. (decomp.). The free base melts at 44°–45° C.

In analogous manner, from ethyl 4-[2-(piperazin-1-yl)-ethyl]-benzoate, there are prepared the following products:

(23a) with ethyl α-bromopropioniate
 ethyl 4-{2-[1-(1-ethoxycarbonylethyl)-piperazin-4-yl]-ethyl}-benzoate
 Yield 94% of theory; viscous oil
(23b) with 1-n-hexadecyl bromide:
 ethyl 4-[2-(1-n-hexadecylpiperazin-4-yl)-ethyl]-benzoate
 Yield 61% of theory; m.p. 54°–56° C. (recrystallised from acetone)
(23c) with 4-chlorobenzyl chloride:
 ethyl 4-{2-[1-(4-chlorobenzyl)-piperazin-4-yl]-ethyl}-benzoate
 Yield 93% of theory; m.p. 44°–45° C.
(23d) with 2-phenoxyethyl bromide:
 ethyl 4-{2-[1-(2-phenoxyethyl)-piperazin-4-yl]-ethyl}-benzoate
 Yield 96% of theory of hydrochloride; m.p. 256° C.
(23e) with 2-(4-chlorophenoxy)-propyl bromide:
 ethyl 4-{2-[1-(2-(4-chlorophenoxy)-propyl)-piperazin-4-yl]-ethyl}-benzoate
 Yield 72% of theory of hydrochloride; m.p. 250°–253° C. (recrystallised from methanol)
(23f) with 2-(4-methoxyphenoxy)-propyl bromide:
 ethyl 4-{2-[1-(2-(4-methoxyphenoxy)-propyl)-piperazin-4-yl]-ethyl}-benzoate
 Yield 79% of theory of hydrochloride; m.p. 243°–246° C. (recrystallised from methanol)
(23g) with 2-(4-nitrophenoxy)-propyl bromide:
 1-(4-ethoxycarbonylphenethyl)-4-[2-(4-nitrophenoxy)-propyl]-piperazine
 Yield 73% of theory of dihydrochloride; m.p. 249°–250° C. (recrystallised from aqueous ethanol)
(23h) with 2-(4-cyanophenoxy)-propyl bromide:
 1-(4-ethoxycarbonylphenethyl)-4-[2-(4-cyanophenoxy)-propyl]-piperazine
 Yield 66% of theory of dihydrochloride; m.p. 243°–244° C. (recrystallised from aqueous ethanol)
(23i) with 3-chlorobenzyl chloride:
 ethyl 4-{2-[1-(3-chlorobenzyl)-piperazin-4-yl]-ethyl}-benzoate
 Yield 84% of theory of dihydrochloride; m.p. 259°–260° C. (recrystallised from ethanol containing a few drops of dilute hydrochloric acid)
(23j) with 3-trifluoromethylbenzyl chloride:
 ethyl 4-{2-[1-(3-trifluoromethylbenzyl)-piperazin-4-yl]-ethyl}-benzoate
 Yield 75% of theory of dihydrochloride; m.p. 249°–251° C. (recrystallised from ethanol and 2N hydrochloric acid)
(23k) with 4-fluorobenzyl chloride:
 ethyl 4-{2-[1-(4-fluorobenzyl)-piperazin-4-yl]-ethyl}-benzoate
 Yield 73% of theory of dihydrochloride; m.p. 293° C. (decomp.) (recrystallised from ethanol and 2N hydrochloric acid)
(23l) with 3-trifluoromethylphenethyl chloride:
 ethyl 4-{2-[1-(3-trifluoromethylphenethyl)-piperazin-4-yl]-ethyl}-benzoate
 Yield 77% of theory of sulphate; m.p. 256°–258° C. (recrystallised from water)
(23m) with 3,4-dichlorocinnamyl chloride:
 ethyl 4-{2-[1-(3,4-dichlorocinnamyl)-piperazin-4-yl]-ethyl}-benzoate
 Yield 62% of theory of dihydrochloride; m.p. 245° C. (decomp.) (recrystallised from ethanol).

EXAMPLE 24

Analogously to Example 23 but using acetonitrile instead of butan-2-one, from ethyl 4-[2-(piperazin-1-yl)-ethyl]-benzoate and 4-chlorophenacyl bromide there is obtained at 20° C. ethyl 4-{2-[1-(4-chlorophenacyl)-piperazin-4-yl]-ethyl}-benzoate. Yield 67% of theory of hydrochloride; m.p. 251°–253° C.

EXAMPLE 25

Ethyl 4-{2-[1-(4-chlorocinnamyl)-piperazin-4-yl]-ethyl}-benzoate

A mixture of 33.5 g. (0.1 mole) ethyl 4-[2-piperazin-1-yl)-ethyl]-benzoate dihydrochloride, 19.6 g. (105 mmole) 4-chlorocinnamyl chloride, 40.8 g. (0.4 mole) anhydrous triethylamine and 400 ml. anhydrous tetrahydrofuran is maintained at reflux temperature for 24 hours and subsequently evaporated in a vacuum. The residue is mixed with methylene chloride and water. After vigorous mixing up, the phases are separated. The methylene chloride phase is washed several times with water, then dried with anhydrous sodium sulphate and evaporated. The residue is dissolved in a little methylene chloride and hydrogen chloride-containing diethyl ether, whereupon the dihydrochloride precipitates out. This is filtered off with suction, washed with diethyl ether, digested with hot ethanol and finally dried to give 39.5 g. of the dihydrochloride of the desired compound; m.p. 283°–285° C.

In an analogous manner and with the use of ethyl 4-[(piperazin-1-yl)-methyl]-benzoate dihydrochloride as starting material, there is prepared the following compounds:

(25a) with 4-chlorocinnamyl chloride:
 ethyl 4-[1-(4-chlorocinnamyl)-piperazin-4-ylmethyl]-benzoate
 Yield 84% of theory of dihydrochloride; m.p. 241°–241.5° C.

Again in an analogous manner but with the use of ethyl 4-[2-(piperazin-1-yl)-ethyl]-benzoate dihydrochloride as starting material, there are prepared the following compounds:

(25b) with 2-(4-cyanophenoxy)-propyl bromide:
 1-(4-ethoxycarbonylphenethyl)-4-[2-(4-cyanophenoxy)-propyl]-piperazine
 Yield 69% of theory of dihydrochloride: m.p. 243°–244° C. (recrystallised from aqueous ethanol)

(25c) with 2-chlorocinnamyl chloride:
ethyl 4-{2-[1-(2-chlorocinnamyl)-piperazin-4-yl]-ethyl}-benzoate
Yield 89% of theory of dihydrochloride; m.p. 262°–264° C. (recrystallised from ethanol)

(25d) with 3-bromocinnamyl chloride:
ethyl 4-{2-[1-(3-bromocinnamyl)-piperazin-4-yl]-ethyl}-benzoate
Yield 89% of theory of dihydrochloride; m.p. 277°–278° C.

(25e) with 4-nitrocinnamyl chloride:
ethyl 4-{2-[1-(4-nitrocinnamyl)-piperazin-4-yl]-ethyl}-benzoate
Yield 91% of theory of dihydrochloride; m.p. 256°–259° C.

(25f) with 4-cyanocinnamyl bromide:
ethyl 4-{2-[1-(4-cyanocinnamyl)-piperazin-4-yl]-ethyl}-benzoate
Yield 65% of theory; m.p. 99°–100° C. (recrystallised from isooctane)

(25g) with 3-methoxycinnamyl chloride:
ethyl 4-{2-[1-(3-methoxycinnamyl)-piperazin-4-yl]-ethyl}-benzoate
Yield 96% of theory of dihydrochloride; m.p. 265°–267° C.

(25h) with 3-trifluoromethylcinnamyl chloride:
ethyl 4-{2-[1-(3-trifluoromethylcinnamyl)-piperazin-4-yl]-ethyl}-benzoate
Yield 87% of theory of dihydrochloride; m.p. 272°–275° C.

From ethyl 4-[3-(piperazin-1-yl)-propyl]-benzoate dihydrochloride, there can also be prepared the following compound in an analogous manner:

(25i) with 4-chlorocinnamyl chloride:
ethyl 4-{3-[1-(4-chlorocinnamyl)-piperazin-4-yl]-propyl}-benzoate
Yield 76% of theory of dihydrochloride; m.p. 245°–247° C. (recrystallised from aqueous ethanol).

From ethyl 4-(piperazin-1-yl)-phenylacetate, the following compound can also be prepared in an analogous manner:

(25j) with 4-chlorocinnamyl chloride:
ethyl 4-[1-(4-chlorocinnamyl)-piperazin-4-yl]-phenylacetate
Yield 67% of theory of dihydrochloride; m.p. 200°–201° C. (recrystallised from glacial acetic acid)

EXAMPLE 26

Ethyl 4-{2-[1-(3-phenylpropyl)-piperazin-4-yl]-ethyl}-benzoate

A mixture of 40 ml. HMPT, 23.6 g. (90 mmole) ethyl 4-[2-(piperazin-1-yl)-ethyl]-benzoate and 8.96 g. (45 mmole) 3-bromopropylbenzene is maintained at 110° C. for 22 hours, whereby, immediately after mixing together, the temperature increases to about 55° C. and the formation of a pale precipitate is observed. At 110° C., a clear, red-brown solution is present, from which, upon cooling, a product crystallises out. It is poured into a little water, extracted with diethyl ether, the ether phase is washed with water, dried with anhydrous sodium sulphate and evaporated. The crude product is dissolved in diethyl ether and converted into the dihydrochloride by means of hydrogen chloride-containing diethyl ether and recrystallised from ethanol containing 2 drops of concentrated hydrochloric acid; m.p. 273° C. (decomp.). Yield 76% of theory.

EXAMPLE 27

Ethyl 4-{2-[1-(4-chlorophenylacetyl)-piperazin-4-yl]-ethyl}-benzoate

To a mixture of 9.7 g. (37 mmole) ethyl 4-[2-(piperazin-1-yl)-ethyl]-benzoate, 40 ml. methylene chloride and 6.3 g. (80 mmole) anhydrous pyridine is added dropwise at 0° C., in the course of 40 minutes, a solution of 7.0 g. (37 mmole) 4-chlorophenylacetyl chloride in 20 ml. methylene chloride, a cheesy precipitate being formed. After stirring at 20° C. for 4 hours, the reaction mixture is poured into 250 ml. ice water, rendered alkaline with ammonia and extracted several times with methylene chloride. The methylene chloride solution is washed twice with water, dried with anhydrous sodium sulphate and evaporated. After the addition of ligroin, crystallisation occurs. The product is recrystallised from diethyl ether to give 51% of theory of the desired product; m.p. 88°–89° C.

Analogously thereto, from ethyl 4-[2-(piperazin-1-yl)-ethyl]-benzoate dihydrochloride, the following compounds are obtained:

(27a) with 4-chlorobenzoyl chloride:
ethyl 4-{2-[1-(4-chlorobenzoyl)-piperazin-4-yl]-ethyl}-benzoate
Yield 71% of theory; m.p. 80°–82° C. (recrystallised from ethyl acetate/ligroin)

(27b) with 4-chlorocinnamoyl chloride:
ethyl 4-{2-[1-(4-chlorocinnamoyl)-piperazin-4-yl]-ethyl}-benzoate
Yield 68% of theory; m.p. 114°–116° C. (recrystallised from ethanol/ligroin).

EXAMPLE 28

Ethyl 4-{2-[1-(3,5-di-tert.-butyl-4-hydroxycinnamoyl)-piperazin-4-yl]-ethyl}-benzoate To a mixture of 16.8 g. (50 mmole) ethyl 4-[2-(piperazin-1-yl)-ethyl]-benzoate dihydrochloride and 200 ml. anhydrous pyridine is added dropwise at 5°–10° C., in the course of 40 minutes, a solution of 14.8 g. 3,5-di-tert.-butyl-4-hydroxycinnamoyl chloride and 50 ml. anhydrous benzene. The reaction mixture is stirred for 4 hours at 20° C., the benzene and pyridine are substantially distilled off in a vacuum and the residue is stirred into about 1 liter ice water. The separated, greasy precipitate is taken up in methylene chloride and the methylene chloride phase is washed with aqueous sodium carbonate solution, dried with anhydrous sodium sulphate and evaporated to dryness in a vacuum. The crude base is dissolved in ethanol, gassed with hydrogen chloride and finally precipitated as the hydrochloride by the addition of diethyl ether. The yield is 17.3 g. (62% of theory) of the desired product which, after stirring up with diethyl ether, melts at 193°–195° C. (decomp.).

EXAMPLE 29

Ethyl 4-{2-[1-(3-(3,5-di-tert.-butyl-4-hydroxyphenyl)-propionyl)-piperazin-4-yl]-ethyl}-benzoate This is prepared analogously to Example 12 from ethyl 4-[2-(piperazin-1-yl)-ethyl]-benzoate, 3-(3,5-di-tert.-butyl-4-hydroxyphenyl)-propionic acid, phosphorus trichloride and pyridine. Yield 62% of theory; m.p. 105°–107° C. (recrystallised from ethyl acetate/ligroin).

EXAMPLE 30

Ethyl 4-[2-(1-benzenesulphonylpiperazin-4-yl)-ethyl]-benzoate

To a solution of 16.75 g. (50 mmole) ethyl 4-[2-(piperazin-1-yl)-ethyl]-benzoate dihydrochloride and 250 ml. anhydrous pyridine, there is added dropwise, at 10°–15° C. and with vigorous stirring, 8.83 g. (50 mmole) benzenesulphochloride. After standing at 20° C. for 24 hours, 2/3 of the pyridine is stripped off in a vacuum, the residue is stirred into ice water and the separated precipitate is filtered off with suction. After washing with water and drying, it is recrystallised from ethyl acetate to give 17.6 g. (88% of theory) of the desired product; m.p. 156°–157° C.

In analogous manner, from ethyl 4-[2-(piperazin-1-yl)-ethyl]-benzoate, there are obtained:
(30a) with tosyl chloride:
  ethyl 4-{2-[1-(p-toluenesulphonyl)-piperazin-4-yl]-ethyl}-benzoate
  Yield 80% of theory; m.p. 141° C. (recrystallised from ethyl acetate)
(30b) with methanesulphonyl chloride:
  ethyl 4-[2-(1-methanesulphonylpiperazin-4-yl)-ethyl]-benzoate
  Yield 87% of theory; m.p. 132°–134° C. (recrystallised from ethyl acetate/ligroin)
(30c) with 4-chlorobenzenesulphonyl chloride:
  ethyl 4-{2-[1-(4-chlorobenzenesulphonyl)-piperazin-4-yl]-ethyl}-benzoate
  Yield 70% of theory; m.p. 148°–150° C. (recrystallised from ethyl acetate/ligroin)

EXAMPLE 31

Ethyl 4-{2-[1-(Acetophenone-2-sulphonyl)-piperazin-4-yl]-ethyl}-benzoate

To a solution of 24.2 g. (92 mmole) ethyl 4-[2-(piperazin-1-yl)-ethyl]-benzoate in 65 ml. anhydrous diethyl ether there is added dropwise, with stirring and ice cooling, a solution of 10.1 g. (46 mmole) ω-acetophenone sulphonyl chloride in 260 ml. anhydrous diethyl ether. Stirring is continued for 2 hours at 20° C. and the reaction mixture then left to stand for 3 days, whereafter it is mixed with water and vigorously shaken. The ether phase is separated off and the aqueous phase back-extracted three times with ethyl acetate. The combined ethyl acetate extracts are, together with the ether phase, dried and evaporated and the residue is recrystallised twice from ethanol to give 8.0 g. (39% of theory) of the desired compound; m.p. 115°–117° C.

EXAMPLE 32

3-[1-(4-Ethoxycarbonylphenethyl)-piperazin-4-yl]-propanesulphonic acid

To a solution of 10.25 g. (39 mmole) ethyl 4-[2-(piperazin-1-yl)-ethyl]-benzoate and 70 ml. anhydrous ethanol, there are added 4.76 g. (39 mmole) 1,3-propanesultone, followed by stirring at 20° C. After standing overnight, the ethanol is stripped off and the residue is treated with diethyl ether and ligroin. After suction filtration, it is recrystallised from ethanol to give 11.2 g. (75% of theory) of the desired compound; m.p. 235°–236° C.

EXAMPLE 33

4-{2-[1-(3-Phenylpropyl)-piperazin-4-yl]-ethyl}-benzoic acid

A mixture of 14.1 g. (31 mmole) ethyl 4-{2-[1-(3-phenylpropyl)-piperazin-4-yl]-ethyl}-benzoate dihydrochloride, 100 ml. ethanol and 100 ml. 1N potassium hydroxide solution is maintained at 50° C. for 2 hours and then the ethanol is distilled off in a vacuum. After acidification with hydrochloric acid, the dihydrochloride precipitates out. It is filtered off with suction, washed with 1N hydrochloric acid and dried. Yield: 10.5 g. (96% of theory) of the dihydrochloride of the desired compound; m.p. 303° C. (decomp.).

In analogous manner, there are prepared:
(33a) 4-{2-[1-(1-carboxyethyl)-piperazin-4-yl]-ethyl}-benzoic acid
  Yield 63% of theory; m.p. 273°–276° C.
  hydrochloride: m.p. 252°–255° C.
(33b) 4-{2-[1-(4-chlorobenzyl)-piperazin-4-yl]-ethyl}-benzoic acid
  Yield 76% of theory; m.p. 195°–197° C. (recrystallised from methanol)
  dihydrochloride: m.p. >260° C.
(33c) 4-{2-[1-(2-phenoxyethyl)-piperazin-4-yl]-ethyl}-benzoic acid
  Yield 86% of theory; m.p. 208°–210° C. dihydrochloride: m.p. 265°–268° C.
(33d) 4-{2-[1-(2-phenoxypropyl)-piperazin-4-yl]-ethyl}-benzoic acid
  Yield 62% of theory of hydrochloride; m.p. 245°–248° C.
  (recrystallised from ethanol)
(33e) 4-{2-[1-(2-(4-chlorophenoxy)-propyl)-piperazin-4-yl]-ethyl}-benzoic acid
  Yield 84% of theory; m.p. 183° C.
  dihydrochloride: m.p. 246°–249° C.
(33f) 4-{2-[1-(2-(4-methoxyphenoxy)-propyl)-piperazin-4-yl]-ethyl}-benzoic acid
  Yield 69% of theory; m.p. 128°–130° C.
  dihydrochloride: m.p. 246°–249° C.
(33g) 4-{2-[1-(2-(4-methylphenoxy)-propyl)-piperazin-4-yl]-ethyl}-benzoic acid
  Yield 71% of theory of hydrochloride; m.p. 147°–148° C.
  (recrystallised from aqueous ethanol)
(33h) 4-{2-[1-(4-chlorophenyl)-piperazin-4-yl]-ethyl}-benzoic acid
  Yield 87% of theory of hydrochloride monohydrate; m.p. 275° C. (recrystallised from aqueous ethanol)
(33i) 4-{2-[1-(4-chlorobenzoyl)-piperazin-4-yl]-ethyl}-benzoic acid
  Yield 80% of theory; m.p. 85°–87° C.
  hydrochloride: m.p. 294°–296° C.
(33j) 4-{2-[1-(4-chlorocinnamoyl)-piperazin-4-yl]-ethyl}-benzoic acid
  Yield 84% of theory; m.p. 243°–244° C.
(33k) 4-{2-[1-(3,5-di-tert.-butyl-4-hydroxycinnamoyl)-piperazin-4-yl]-ethyl}-benzoic acid
  Yield 88% of theory; m.p. 233° C.
(33l) 4-{2-[1-(3-(3,5-di-tert.-butyl-4-hydroxyphenyl)-propionyl)-piperazin-4-yl]-ethyl}-benzoic acid
  Yield 77% of theory; m.p. 93°–95° C.
  hydrochloride: m.p. 230°–231° C.

(33 m) 4-{2-[1-(methanesulphonyl)-piperazin-4-yl]-ethyl}-benzoic acid
Yield 71% of theory of hydrochloride; m.p. 274°-276° C.
(recrystallised from aqueous acetone)
(33 n) 4-{2-[1-(benzenesulphonyl)-piperazin-4-yl]-ethyl}-benzoic acid
Yield 96% of theory; m.p. 266°-267° C.
(33 o) 4-{2-[1-(4-chlorobenzenesulphonyl)-piperazin-4-yl]-ethyl}-benzoic acid
Yield 71% of theory of hydrochloride; m.p. 273°-275° C.
(recrystallised from ethanol)
(33 p) 4-{2-[1-(methylbenzenesulphonyl)-piperazin-4-yl]-ethyl}-benzoic acid
Yield 97% of theory of hydrochloride; m.p. 298° C.
(33 q) 4-{2-[1-(acetophenone-2-sulphonyl)-piperazin-4-yl]-ethyl}-benzoic acid
Yield 77% of theory of hydrochloride; m.p. 232° C. (recrystallised from ethanol)
(33 r) 4-{2-[1-(4-phenoxyphenyl)-piperazin-4-yl]-ethyl}-benzoic acid
Yield 88% of theory of hydrochloride; m.p. 296° C.
(33s) 4-{2-[1-(4-benzyloxyphenyl)-piperazin-4-yl]-ethyl}-benzoic acid
Yield 87% of theory; m.p. 234°-235° C.
(33t) 4-{2-[1-(2-methyl-3-phenylpropionyl)-piperazin-4-yl]-ethyl}-benzoic acid
Yield 94% of theory of hydrochloride; m.p. 222.5°-223° C.
(33u) 4-{2-[1-(3-(4-chlorophenyl)-2-methylpropyl)-piperazin-4-yl]-ethyl}-benzoic acid
Yield 88% of theory of dihydrochloride; m.p. 277°-278° C. (recrystallised from water)
(33v) 4-{2-[1-(3-trifluoromethylphenethyl)-piperazin-4-yl]-ethyl}-benzoic acid
Yield 95% of theory of sulphate; m.p. 283°-285° C. (recrystallised from 60% acetic acid)
(33w) 4-{2-[1-(3,4-dichlorocinnamyl)-piperazin-4-yl]-ethyl}-benzoic acid
Yield 76% of theory of dihydrochloride; m.p. 295° C. (recrystallised from aqueous ethanol)

EXAMPLE 34

4-{2-[1-Phenethylpiperazin-4-yl]-ethyl}-benzoic acid

A mixture of 9.0 g. (20.5 mmole) ethyl 4-{2-[1-phenethylpiperazin-4-yl]-ethyl}-benzoate dihydrochloride and 100 ml. 6N hydrochloric acid is maintained at reflux temperature for 20 hours, while stirring. It is then cooled, suction filtered and the precipitate washed with cold 6N hydrochloric acid and dried. Yield 6.6 g. of the desired product as dihydrochloride; m.p. 317° C. (decomp.).

If the starting ester is very difficult to dissolve, the addition of some ethanol to the hydrolysis mixture is recommended.

Analogously to this example, there are prepared:
(34a) 4-{2-[1-(2-hydroxypropyl)-piperazin-4-yl]-ethyl}-benzoic acid
Yield 87% of theory of dihydrochloride; m.p. 289° C. (recrystallised from ethanol/concentrated hydrochloric acid)
(34b) 4-{2-[1-(4-methoxybenzyl)-piperazin-4-yl]-ethyl}-benzoic acid
Yield 79% of theory of dihydrochloride; m.p. 286° C. (recrystallised from aqueous ethanol)
(34c) 4-{2-[1-(4-chlorocinnamyl)-piperazin-4-yl]-ethyl}-benzoic acid
Yield 71% of theory of dihydrochloride; m.p. 288° C. (recrystallised from water)
The sulphate melts at 299° C.
(34d) 4-{2-[1-methylpiperazin-4-yl]-ethyl}-benzoic acid
Yield 70% of theory of dihydrochloride; m.p. 298° C.
(34e) 3-[1-(4-carboxyphenethyl)-piperazin-4-yl]-propanesulphonic acid
Yield 96% of theory of hydrochloride; m.p. 298° C.
(34f) 4-[1-(4-chlorocinnamyl)-piperazin-4-ylmethyl]-benzoic acid
Yield 73% of theory of dihydrochloride; m.p. 249°-250° C.
(recrystallised from aqueous ethanol)
(34g) 4-[2-(piperazin-1-yl)-ethyl]-benzoic acid
Yield 87%. of theory of dihydrochloride; m.p. 285°-287° C.
(recrystallised from 2N hydrochloric acid)
(34h) 4-[2-(1-benzylpiperazin-4-yl)-ethyl]-benzoic acid
Yield 84% of theory of dihydrochloride; m.p. 272°-274° C.
(recrystallised from 2N hydrochloric acid)
(34i) 4-{2-[1-(2-chlorobenzyl)-piperazin-4-yl]-ethyl}-benzoic acid
Yield 87% of theory of dihydrochloride; m.p. 287°-290° C.
(recrystallised from aqueous ethanol)
(34j) 4-{2-[1-(4-fluorobenzyl)-piperazin-4-yl]-ethyl}-benzoic acid
Yield 82% of theory of dihydrochloride; m.p. 311° C.
(recrystallised from 2N hydrochloric acid
(34k) 4-{2-[1-(3-chlorobenzyl)-piperazin-4-yl]-ethyl}-benzoic acid
Yield 87% of theory of dihydrochloride; m.p. 294° C.
(recrystallised from aqueous acetone)
(34l) 4-{2-[1-(3-trifluoromethylphenyl)-piperazin-4-yl]-ethyl}-benzoic acid
Yield 73% of theory of dihydrochloride; m.p. 242°-243° C.
(recrystallised from aqueous ethanol)
(34m) 4-{2-[1-(2-chlorocinnamyl)-piperazin-4-yl]-ethyl}-benzoic acid
Yield 85% of theory of dihydrochloride; m.p. 280°-281° C.
(recrystallised from dilute hydrochloric acid)
(34n) 4-{2-[1-(3-bromocinnamyl)-piperazin-4-yl]-ethyl}-benzoic acid
Yield 78% of theory of dihydrochloride; m.p. 282°-283° C.
(recrystallised from dilute hydrochloric acid)
(34o) 4-{2-[1-(4-nitrocinnamyl)-piperazin-4-yl]-ethyl}-benzoic acid
Yield 85% of theory of dihydrochloride; m.p. 273°-274° C.
(recrystallised from dilute hydrochloric acid).
Light sensitive.
(34p) 4-{2-[1-(3-methoxycinnamyl)-piperazin-4-yl]-ethyl}-benzoic acid
Yield 72% of theory of dihydrochloride; m.p. >254° C.
(recrystallised from dilute hydrochloric acid)
(34q) 4-{2-[1-(3-trifluoromethylcinnamyl)-piperazin-4-yl]-ethyl}-benzoic acid
Yield 79% of theory of dihydrochloride; m.p. 281°-282° C.

(recrystallised from dilute hydrochloric acid)
(34r) 4-{2-[1-(3-trifluoromethylbenzyl)-piperazin-4-yl]-ethyl}-benzoic acid
Yield 96% of theory of dihydrochloride; m.p. 262°-264° C.
(recrystallised from aqueous acetone)
(34s) 1-(4-carboxyphenethyl)-4-[2-(4-nitrophenoxy)-propyl]-piperazine
Yield 66% of theory of dihydrochloride; m.p. 274°-276° C.
(recrystallised from aqueous ethanol)
(34t) 1-(4-carboxyphenethyl)-4-[2-(4-aminophenoxy)-propyl]-piperazine
Yield 82% of theory of dihydrochloride; m.p. 254°-255° C.
(recrystallised from aqueous ethanol)
(34u) 4-{2-[1-(2-methyl-3-phenylpropyl)-piperazin-4-yl]-ethyl}-benzoic acid
Yield 81% of theory of dihydrochloride; m.p. 261°-263° C.
(recrystallised from dilute hydrochloric acid)
(34v) 4-{3-[1-(4-chlorocinnamyl)-piperazin-4-yl]-propyl}-benzoic acid
Yield 78% of theory of dihydrochloride; m.p. 276°-277° C.
(recrystallised from dilute hydrochloric acid)
(34w) 4-[3-(piperazin-1-yl)-propyl]-benzoic acid
Yield 86% of theory of dihydrochloride; m.p. 264°-265° C.
(recrystallised from dilute hydrochloric acid)
(34x) 4-[3-(1-benzylpiperazin-4-yl)-propyl]-benzoic acid
Yield 83% of theory of dihydrochloride; m.p. 275°-276° C.
(recrystallised from dilute hydrochloric acid)
(34y) 4-[1-(4-chlorocinnamyl)-piperazin-4-yl]-phenylacetic acid
Yield 76% of theory of hydrochloride; m.p. 219°-220° C.
(recrystallised from acetic acid)
(34z) 4-(piperazin-1-yl)-benzoic acid
Yield 82% of theory of hydrochloride; m.p. 322° C.
(recrystallised from water).

EXAMPLE 35

Ethyl 4-(piperazin-1-yl)-phenylacetate

A mixture of 100 g. (0.568 mole) p-aminophenylacetic acid, 99.6 g. (0.568 mole) bis-(2-chloroethyl)-amine hydrochloride and 350 ml. n-butanol is heated at reflux temperature for 120 hours, while stirring. 39.2 g. (0.284 mole) Potassium carbonate are then added thereto and heating at reflux temperature continued for a further 145 hours. Subsequently, the reaction mixture is suction filtered while hot to remove insolubles and the filtrate is evaporated. The residue is taken up in water, rendered strongly alkaline with 10N aqueous sodium hydroxide solution and the organic components are extracted with diethyl ether. The ether extracts are evaporated and the residue is dissolved in ethanol. From this solution, ethyl 4-(piperazin-1-yl)-phenylacetate is precipitated as the sulphate by adding about 40 ml. concentrated sulphuric acid. Yield 120 g. (61% of theory); m.p. 194°-197° C.

In analogous manner, with the use of n-butyl 4-aminophenylacetate, there is prepared n-butyl 4-(piperazin-1-yl)-phenylacetate; yield 52% of theory of sulphate; m.p. 197°-199° C.

EXAMPLE 36

Analogously to Example 23, by the reaction of ethyl 4-(piperazin-1-yl)-phenylacetate with the appropriate alkyl halides in butan-2-one in the presence of anhydrous potassium carbonate, there are prepared the following compounds:
(36a) with 1-n-hexadecyl bromide:
ethyl 4-[1-(1-n-hexadecyl)-piperazin-4-yl]-phenylacetate
Yield 79% of theory; from an isopropanol-water mixture amorphous powder
(36b) with 4-chlorobenzyl chloride
ethyl 4-[1-(4-chlorobenzyl)-piperazin-4-yl]-phenylacetate
Yield 92% of theory; viscous oil
(36c) with 2-phenoxypropyl bromide
ethyl 4-[1-(2-phenoxypropyl)-piperazin-4-yl]-phenylacetate
Yield 70% of theory of dihydrochloride; m.p. 153°-154° C.

EXAMPLE 37 n-Butyl 4-[1-(3,5-di-tert.-butyl-4-hydroxyphenethyl)-piperazin-4-yl]-phenylacetate A mixture of 20.2 g. (50 mmole) of the tosylate of 3,5-di-tert.-butyl-4-hydroxyphenethyl alcohol, 13.8 g. (50 mmole) n-butyl 4-(piperazin-1-yl)-phenylacetate, 6.9 g. (50 mmole) powdered anhydrous potassium carbonate and 200 ml. butan-2-one is maintained at reflux temperature for 24 hours, then suction filtered hot and the filtrate evaporated in a vacuum. The residue is taken up in diethyl ether, the ether phase is extracted twice with water, then dried with anhydrous sodium sulphate and evaporated. By means of ligroin, the product is brought to crystallisation and recrystallised from n-butanol. Yield 14.3 g. (59% of theory); m.p. 103°-105° C.

EXAMPLE 38

By the reaction of ethyl or n-butyl 4-(piperazin-1-yl)-phenylacetate in pyridine analogously to Example 17, the following compounds are obtained:
(38a) with 4-chlorobenzoyl chloride:
n-butyl 4-[1-(4-chlorobenzoyl)-piperazin-4-yl]-phenylacetate
Yield 79% of theory of hydrochloride; m.p. 202°-204° C.
(recrystallised from n-butanol)
(38b) with 4-chlorocinnamoyl chloride:
ethyl 4-[1-(4-chlorocinnamoyl)-piperazin-4-yl]-phenylacetate
Yield 69% of theory; m.p. 137°-139° C.
hydrochloride: m.p. 203°-206° C.

EXAMPLE 39 n-Butyl 4-[1-(4-chlorophenyl)-piperazin-4-yl]-phenylacetate

This is obtained analogously to Example 35 by the reaction of 4-chloro-N,N-bis-(2-chloroethyl)-amine with n-butyl 4-aminophenylacetate in n-butanol in the presence of potassium carbonate. After suction filtration from potassium carbonate and potassium chloride at an elevated temperature, the product precipitates out from the filtrate. Yield 66% of theory; m.p. 99°-100° C. (recrystallised from n-butanol).

EXAMPLE 40

Ethyl 4-[1-(benzenesulphonyl)-piperazin-4-yl]-phenylacetate

This is obtained by the reaction of ethyl 4-(piperazin-1-yl)-phenylacetate with benzenesulphochloride analogously to Example 30. Yield 85% of theory; m.p. 160°–163° C.

EXAMPLE 41

4-[2-(Piperazin-1-yl)-ethyl]-phenylacetic acid (a) A mixture of 17.6 g. (0.1 mole) 1-benzylpiperazine, 100 ml. anhydrous tetrahydrofuran, 22.8 g. (0.1 mole) 4'-(2-bromoethyl)-acetophenone and 21 g. (0.21 mole) triethylamine is kept under reflux for 8 hours, then cooled and the precipitated hydrobromide removed by suction filtration. Anhydrous diethyl ether is added thereto, subsequently precipitated hydrobromide is removed by suction filtration and the filtrate mixed, while cooling, with a sufficient amount of hydrogen chloride-containing diethyl ether. The precipitated hydrochloride is filtered off with suction, washed with diethyl ether and dried. Yield 32.5 g. (82% of theory) 1-(4-acetylphenethyl)-4-benzylpiperazine dihydrochloride; m.p. 253°–255° C.

This starting material can also be prepared in the following way:

A mixture of 22.7 g. (0.1 mole) 4'-(2-bromoethyl)-acetophenone, 50 ml. ethanol and 17.6 g. (0.1 mole) 1-benzylpiperazine is heated for 16 hours at reflux temperature, 10.0 g. powdered sodium carbonate are added thereto and the reaction mixture further heated for 8 hours. It is then evaporated and the residue dissolved in dilute hydrochloric acid, followed by extraction with diethyl ether, whereafter the aqueous phase is rendered alkaline with 10% aqueous sodium hydroxide solution. It is now again extracted with diethyl ether, the ether phase is dried with potassium hydroxide and finally, by the addition of hydrogen chloride-containing diethyl ether, the dihydrochloride of 1-(4-acetylphenethyl)-4-benzylpiperazine is precipitated out. After washing with diethyl ether and drying, the yield obtained is 32.4 g. (82% of theory); m.p. 249°–253° C.

(b) A mixture of 20 g. (50 mmole) 1-(4-acetylphenethyl)-4-benzylpiperazine, 3.2 g. (0.1 mole) sulphur and 30 ml. (0.35 mole) morpholine is maintained for 20 hours at 135° C., then cooled, poured into water and extracted with diethyl ether. The ether phase is washed three times with water, dried with anhydrous magnesium sulphate, treated with active charcoal and suction filtered. The filtrate is mixed with a sufficient amount of hydrogen chloride-containing diethyl ether. It is then suction filtered, washed with diethyl ether and dried. Yield 13.9 g. (44% of theory) 4-[2-(1-benzylpiperazin-4-yl)-ethyl]-phenylacetic acid thiomorpholide dihydrochloride; m.p. 235°–237° C.

(c) A mixture of 10.0 g. (20 mmole) of the thiomorpholide dihydrochloride and 100 ml. 6N hydrochloric acid is boiled for 5 hours, then concentrated to half its volume and cooled. The product is removed by suction filtration, washed with a little cold 2N hydrochloric acid and recrystallised from water. Yield 5.1 g. (61% of theory) of the dihydrochloride of 4-[2-(1-benzylpiperazin-4-yl)-ethyl]-phenylacetic acid; m.p. 244°–245° C. (decomp.).

(d) 140 g. (0.34 mole) of the dihydrochloride of 4-[2-(1-benzylpiperazin-4-yl)-ethyl]-phenylacetic acid is dissolved in a mixture of ethanol and 6N hydrochloric acid and 10% palladium-charcoal is added thereto, followed by hydrogenation in a shaker bomb. If the reaction proceeds too slowly, the catalyst is replaced by fresh catalyst. The reaction mixture is then suction filtered and the filtrate is evaporated and brought to crystallisation with some ethyl acetate. Yield 90 g. (82% of theory) of the dihydrochloride of 4-[2-(piperazin-1-yl)-ethyl]-phenylacetic acid; m.p. 238°–239° C. (recrystallised from acetone/water).

EXAMPLE 42

Ethyl 4-[2-(piperazin-1-yl)-ethyl]-phenylacetate

A solution of 83.5 g. (0.26 mole) 4-[2-(piperazin-1-yl)-ethyl]-phenylacetic acid and 850 ml. anhydrous ethanol is gassed from the surface with hydrogen chloride up to saturation, left to stand overnight, then evaporated to half its volume and cooled in an ice bath. The precipitated dihydrochloride is filtered off with suction, washed with some diethyl ether and dried. Yield 85.1 g. (94% of theory); m.p. 258°–260° C. (decomp.).

The following compounds are obtained in an analogous manner:

(42a) n-butyl 4-{2-[1-(2-chlorobenzyl)-piperazin-4-yl]-ethyl}-benzoate from 4-{2-[1-(2-chlorobenzyl)-piperazin-4-yl]-ethyl}-benzoic acid and n-butanol.
Yield 87% of theory.
Dihydrochloride: m.p. 227°–230° C. (recrystallised from n-butanol); and (42b) methyl 4-{2-[1-(4-chlorocinnamyl)-piperazin-4-yl]-ethyl}-benzoate from 4-{2-[1-(4-chlorocinnamyl)-piperazin-4-yl]-ethyl}-benzoic acid and methanol.
Yield 82% of theory.
Dihydrogen sulphate: m.p. 194°–195° C. (recrystallised from butan-2-one/methanol mixture).

EXAMPLE 43

Ethyl 4-{2-[1-(n-hexadecyl)-piperazin-4-yl]-ethyl}-phenylacetate

A mixture of 0.1 mole ethyl 4-[2-(piperazin-1-yl)-ethyl]-phenylacetate dihydrochloride, 250 ml. butan-2-one, 0.2 mole powdered anhydrous potassium carbonate and 0.11 mole 1-n-hexadecyl bromide is maintained at reflux temperature for 16 hours, then filtered with suction and the potassium carbonate/potassium halide mixture washed with warm acetone. The combined organic phases are evaporated and the residue is recrystallised. For the preparation of the dihydrochloride, the evaporation residue is dissolved in diethyl ether, filtered (when necessary) and, while cooling, a sufficient amount of hydrogen chloride-containing diethyl ether is added thereto. The hydrochloride is filtered off with suction, washed with some diethyl ether and dried and then recrystallised from ethanol to which 2 drops of concentrated hydrochloric acid have been added. Yield 60% of theory dihydrochloride; m.p. 282° C.

In an analogous manner, from ethyl 4-[2-(piperazin-1-yl)-ethyl]-phenylacetate, there are prepared the following compounds:

(43a) with 4-chlorobenzyl chloride:
ethyl 4-{2-[1-(4-chlorobenzyl)-piperazin-4-yl]-ethyl}-phenylacetate
reaction time: 1 week; yield 91% of theory of dihydrochloride; m.p. 272°–275° C.

(43b) with phenethyl bromide:

ethyl 4-[2-(1-phenethylpiperazin-4-yl)-ethyl]-phenylacetate
reaction time: 4 days; yield 80% of theory of dihydrochloride; m.p. 264°-266° C.

(43c) with 3-phenylpropyl bromide:
ethyl-{2-[1-(3-phenylpropyl)-piperazin-4-yl]-ethyl}-phenylacetate
reaction time: 40 hours; yield 66% of theory of base (viscous oil)

(43d) with 4-chlorocinnamyl chloride:
ethyl 4-{2-[1-(4-chlorocinnamyl)-piperazin-4-yl]-ethyl}-phenylacetate
reaction time: 40 hours; yield 58% of theory of dihydrochloride; m.p. 282° C. The free base melts at 69° C. (recrystallised from ligroin)

(43e) with 4-methoxybenzyl chloride: ethyl 4-{2-[1-(4-methoxybenzyl)-piperazin-4-yl]-ethyl}-phenylacetate
reaction time: 72 hours; yield 76% of theory of hydrochloride; m.p. 249°-251° C. (recrystallised from ethanol/ligroin)

(43f) with 2-phenoxyethyl bromide:
ethyl 4-{2-[1-(2-phenoxyethyl)-piperazin-4-yl]-ethyl}-phenylacetate
reaction time: 240 hours; yield 87% of theory of hydrochloride; m.p. 238°-240° C.

EXAMPLE 44

Ethyl 4-{2-[1-(3,5-di-tert.-butyl-4-hydroxyphenethyl)-piperazin-4-yl]-ethyl}-phenylacetate A mixture of 13.9 g. (50.2 mmole) p-toluenesulphonic acid (3,5-di-tert.-butyl-4-hydroxyphenethyl)ester, 18.4 g. (45.6 mmole) ethyl 4-[2-(piperazin-1-yl)-ethyl]-phenylacetate, 6.3 g. potassium carbonate and 300 ml. butan-2-one is heated for 8 hours while stirring at reflux temperature. For protection against oxidation, the reaction is carried out under an atmosphere of nitrogen. After cooling, the inorganic precipitate is filtered off with suction, the filtrate is evaporated and the evaporation residue is taken up in diethyl ether. From the ether solution, the hydrochloride is precipitated with hydrogen chloride-containing diethyl ether. After recrystallisation from ethanol, there are obtained 16.4 g. (62% of theory) of the desired compound as hydrochloride; m.p. 247°-250° C.

EXAMPLE 45

Ethyl 4-{2-[1-(2-Hydroxypropyl)-piperazin-4-yl]-ethyl}-phenylacetate

This is prepared analogously to Example 11 by the reaction of ethyl 4-[2-(piperazin-1-yl)-ethyl]-phenylacetate with propylene oxide. Yield 92% of theory; colourless oil.

EXAMPLE 46

4-{2-[1-(4-Chlorophenyl)-piperazin-4-yl]-ethyl}-phenylacetic acid (a) By the reaction of 1-(4-chlorophenyl)-piperazine with 4'-(2-bromoethyl)-acetophenone analogously to Example (41a), there is obtained 4'-{2-[1-(4-chlorophenyl)-piperazin-4-yl]-ethyl}-acetophenone. Yield 64% of theory; m.p. 141°-143° C. (recrystallised from ethyl acetate).

(b) By the reaction of 4'-{2-[1-(4-chlorophenyl)-piperazin-4-yl]-ethyl}-acetophenone with morpholine and sulphur analogously to Example (41b), there is obtained 4-{2-[1-(4-chlorophenyl)-piperazin-4-yl]-ethyl}-phenylacetic acid thiomorpholide hydrochloride.
Yield 81% of theory; m.p. 144°-147° C.

(c) By the saponification of 4-{2-[1-(4-chlorophenyl)-piperazin-4-yl]-ethyl}-phenylacetic acid thiomorpholide with 6N hydrochloric acid (16 hours at reflux temperature), there is obtained, analogously to Example (41c), in 64% yield, the hydrochloride of 4-{2-[1-(4-chlorophenyl)-piperazin-4-yl]-ethyl}-phenylacetic acid; m.p. 241°-243° C.

EXAMPLE 47

By acylation with an acid chloride or by sulphonation with a sulphonic acid chloride according to the following procedure, there are obtained the mentioned compounds:

To a solution of 10.47 g. (30 mmole) ethyl 4-[2-(piperazin-1-yl)-ethyl]-phenylacetate dihydrochloride and 75 ml. anhydrous pyridine, there are added at 5°-10° C., while stirring, 30 mmoles of acyl chloride or sulphonyl chloride and stirring is continued overnight at 20° C. The reaction mixture is then poured into ice water, the precipitate formed is filtered off with suction and washed with aqueous sodium bicarbonate solution and water. After drying, the product is recrystallised.

(47a) with 4-chlorocinnamoyl chloride:
ethyl 4-{2-[1-(4-chlorocinnamoyl)-piperazin-4-yl]-ethyl}-phenylacetate
Yield 68% of theory; m.p. 123°-124° C. (recrystallised from ethyl acetate)

(47 b) with 4-chlorobenzenesulphochloride:
ethyl 4-{2-[1-(4-chlorobenzenesulphonyl)-piperazin-4-yl]-ethyl}-phenylacetate
Yield 71% of theory; m.p. 231°-133° C. (recrystallised from ethanol)

(47 c) with 4-chlorobenzoyl chloride:
ethyl 4-{2-[1-(4-chlorobenzoyl)-piperazin-4-yl]-ethyl}-phenylacetate
Yield 81% of theory; m.p. 126°-128° C.

(47d) with benzenesulphochloride:
ethyl 4-[2-(1-benzenesulphonylpiperazin-4-yl)-ethyl]-phenylacetate
Yield 70% of theory; m.p. 125°-127° C.

EXAMPLE 48

Ethyl 4-{2-[1-(3,5-di-tert.-butyl-4-hydroxycinnamoyl)-piperazin-4-yl]-ethyl}-phenylacetate A solution of 14.0 g. (51 mmole) 3,5-di-tert.-butyl-4-hydroxycinnamic acid and 17.7 g. (51 mmole) ethyl 4-[2-(piperazin-1-yl)-ethyl]-phenylacetate dihydrochloride in 150 ml. anhydrous pyridine is mixed dropwise, with ice cooling, with a solution of 3.57 g. (26 mmole) phosphorus tribromide in 20 ml. pyridine. Stirring is continued for 2 hours, with ice cooling, and the reaction mixture then left to stand for 12 hours at ambient temperature, whereafter it is poured on to ice and extracted with ethyl acetate. The extracts are dried and evaporated, the residue is taken up in diethyl ether and the hydrochloride is precipitated with hydrogen chloride-containing diethyl ether. After recrystallisation from a mixture of ethanol and water, to which has been added some concentrated hydrochloric acid, there are obtained 14.5 g. (47%) of hydrochloride of the desired compound; m.p. 111°-113° C.

In analogous manner, from 3-(3,5-di-tert.-butyl-4-hydroxyphenyl)-propionic acid and ethyl 4-[2-(piperazin-1-yl)-ethyl]-phenylacetate, there is obtained the compound:

(48a) ethyl 4-{2-[1-(3-(3,5-tert.-butyl-4-hydroxyphenyl)-propionyl)-piperazin-4-yl]-ethyl}-phenylacetate Yield 61% of theory; m.p. 116°–117° C. (recrystallised from ethyl acetate);

and from 3,5-di-tert.-butyl-4-hydroxycinnamic acid and methyl 4-(piperazin-1-yl)-phenylacetate the compound:

(48b) methyl 4-[1-(3,5-di-tert.-butyl-4-hydroxycinnamoyl-piperazin-4-yl]-phenylacetate Yield 54% of theory of hydrochloride; m.p. 177°–178° C.

(recrystallised from methanol).

EXAMPLE 49

4-{2-[1-(n-Hexadecyl)-piperazin-4-yl]-ethyl}phenylacetic acid

A mixture of 0.1 mole of the ethyl ester dihydrochloride, 200 ml. 6N hydrochloric acid and 100 ml. dioxan is kept for 3 hours at 80° C., then strongly cooled. The separated crystals are filtered off with suction and recrystallised from aqueous ethanol. Yield 91% of theory of the dihydrochloride of the desirec compound; m.p. 251° C.

In analogous manner, from the corresponding ethyl phenylacetates (or their hydrochlorides), there are obtained the following carboxylic acids:

(49 a) 4-{2-[1-(4-chlorobenzyl-piperazin-4-yl]-ethyl}-phenylacetic acid reaction time: 10 hours (without the addition of dioxan)

yield 65% of theory of dihydrochloride; m.p. 280°–282° C.

(recrystallised from glacial acetic acid)

(49b) 4-[2-(1-phenethylpiperazin-4-yl)-ethyl]-phenylacetic acid reaction time: 10 hours (without the addition of dioxan)

yield 54% of theory of dihydrochloride; m.p. 285°–286° C.

(recrystallised from glacial acetic acid)

(49c) 4-{2-[1-(3-phenylpropyl)-piperazin-4-yl]-ethyl}-phenylacetic acid reaction time: 6 hours (without the addition of dioxane) yield 62% of theory of dihydrochloride; m.p. 248°–251° C.

(recrystallised from glacial acetic acid)

(49d) 4-{2-[1-(4-chlorocinnamoyl-piperazin-4-yl]ethyl}-phenylacetic acid reaction time: 5 hours (with the addition of dioxan)

yield 69% of theory of dihydrochloride; m.p. 273°–274° C.

(recrystallised from acetone/2N hydrochloric acid)

(49e) 4-{2-[1-(4-chlorobenzenesulphonyl)-piperazin-4-yl]-ethyl}-phenylacetic acid reaction time: 35 hours (without the addition of dioxan)

yield 68% of theory of hydrochloride; m.p. 247°–249° C.

(recrystallised from glacial acetic acid).

EXAMPLE 50

As an alternative to Example 49, the saponification of the carboxylic esters can also be carried out, for example, in alkali-containing methanol:

50 mmole carboxylic acid ester are dissolved in 200 ml. methanol and the solution mixed, while stirring, with 100 ml. 1N aqueous potassium hydroxide solution. In the case of hydrochlorides, an additional equivalent amount of aqueous potassium hydroxide solution is added. Heating is continued at 40° C. until no more starting material can be detected by thin layer chromatography. The methanol is now evaporated off and the residue is neutralised with an equivalent amount of hydrochloric acid. If the amino acid does not precipitate out, it is rendered acidic with hydrochloric acid, evaporated to dryness and the hydrochloride separated from inorganic residue by stirring up with ethanol. Oxidation-sensitive esters are saponified under an atmosphere of nitroen.

The following compounds are prepared analogously:

(50a) 4-{2-[1-(2-hydroxypropyl)-piperazin-4-yl]-ethyl}-phenylacetic acid yield 53% of theory; m.p. 176°–178° C.; dihhydrochloride monohydrate: m.p. 224°–227° C.

(50b) 4-{2-[1-(4-methoxybenzyl)-piperazin-4-yl]-ethyl}-phenylacetic acid yield 64% of theory; m.p. 175°–177° C.; dihydrochloride: m.p. 280°–282° C.

(50c) 4-{2-[1-(3,5-di-tert.-butyl-4-hydroxyphenethyl)-piperazin-4-yl]-ethyl}-phenylacetic acid yield 60% of theory; m.p. 210°–213° C.; dihydrochloride monohydrate: m.p. 257°–260° C.

(50d) 4-{2-[1-(2-phenoxyethyl)-piperazin-4-yl]-ethyl}-phenylacetic acid yield 81% of theory; m.p. 143°–145° C.; dihydrochloride: m.p. 214°–217° C.

(50e) 4-{2-[1-(4-chlorobenzoyl)-piperazin-4-yl]-ethyl}-phenylacetic acid yield 69% of theory of hydrochloride; m.p. 228°–230° C.

(50f) 4-{2-[1-(3,5-di-tert.-butyl-4-hydroxycinnamoyl)-piperazin-4-yl]-ethyl}-phenylacetic acid yield 59% of theory of hydrochloride monohydrate; m.p. 164°–167° C.

(50g) 4-{2-[1-(benzenesulphonyl)-piperazin-4-yl]-ethyl}-phenylacetic acid yield 85% of theory; m.p. 184°–186° C.; hydrochloride: m.p. 282°–284° C. and the following 4-(piperazin-1-yl)-phenylacetic acids:

(50h) 4-[1-(n-hexadecyl)-piperazin-4-yl]-phenylacetic acid yield 93% of theory; m.p. 128°–130° C.

(50i) 4-[1-(4-chlorobenzyl)-piperazin-4-yl]-phenylacetic acid yield 63% of theory; m.p. 183° C. (recrystallised from isopropanol)

(50j) 4-[1-(3,5-di-tert.-butyl-4-hydroxyphenethyl)-piperazin-4-yl]-phenylacetic acid yield 71% of theory hydrochloride; m.p. 244°–245° C. (recrystallised from 66% ethanol)

(50k) 4-[1-(2-phenoxypropyl)-piperazin-4-yl]-phenylacetic acid yield 64% of theory; m.p. 156°–158° C.

(50l) 4-[1-(4-chlorobenzoyl)-piperazin-4-yl]-phenylacetic acid yield 77% of theory; m.p. 146°–147° C. (recrystallised from 66% ethanol)

(50m) 4-[1-(4-chlorocinnamoyl)-piperazin-4-yl]-phenylacetic acid yield 69% of theory; m.p. 228°–230° C. (recrystallised from aqueous ethanol)

(50n) 4-[1-(4-chlorophenyl)-piperazin-4-yl]-phenylacetic acid yield 81% of theory; m.p. 210°–212° C.

(50o) 4-[1-(benzenesulphonyl)-piperazin-4-yl]-phenylacetic acid yield 70% of theory; m.p. 128°–130° C.

(50p) 4-[2-(1-benzylpiperazin-4-yl)-propyl]-benzoic acid yield 75% of theory of dihydrochloride; m.p. 277° C. (recrystallised from ethanol/4N hydrochloric acid)

EXAMPLE 51 n-Butyl 3-[4-(piperazin-1-yl)-phenyl]-propionate

A mixture of 175 g. (0.79 mole) n-butyl 3-(-4-aminophenyl)-propionate (prepared by the hydrogenation of n-butyl 4-nitrocinnamate in the presence of palladium-charcoal in n-butanol; b.p. 137°–138° C./0.013 mbar), 141.3 g. (0.79 mole) bis-(2-cholorethyl)-amine hydrochloride and 600 ml. n-butanol is maintained at reflux temperature for 48 hours, then 54.5 g. (0.39 mole) powdered potassium carbonate are added thereto and the reaction allowed to continue for a further 120 hours at the boiling temperature. Thereafter, the reaction mixture is suction filtered hot, the filtrate is evaporated in a vacuum and the oil remaining behind is taken up in n-butanol. The sulphate is now precipitated out in the cold by adding concentrated sulphuric acid. It is filtered off with suction, triturated with diethyl ether and dried. Yield 286.8 g. (69% of theory); m.p. 183°–185° C.

EXAMPLE 52 n-Butyl 3-{4-[1-(2-phenoxypropyl)-piperazin-4-yl]-phenyl}-propionate

A mixture of 21.4 g. (74 mmole) n-butyl 3-[4-(piperazin-1-yl)-phenyl]-propionate, 150 ml. HMPT and 15.8 g. (74 mmole) 2-phenoxypropyl bromide is stirred for 5 hours at 120° C., then poured on to ice water and extracted with ethyl acetate. The extract is evaporated and the evaporation residue dissolved in diethyl ether. The ether solution is dried with anhydrous magnesium sulphate and the hydrochloride is precipitated out with hydrogen chloride-containing diethyl ether. After suction filtration, washing with diethyl ether and drying, the yield is 15.1 g. (44% of theory); m.p. 180°–183° C.

(52a) In an analogous manner, from n-butyl 3-[4-(piperazin-1-yl)-phenyl]-propionate there is prepared, by reaction with n-hexadecyl bromide, n-butyl 3-[4-(1-n-hexadecylpiperazin-4-yl)-phenyl]-propionate; yield 63% of theory of hydrochloride; m.p. 168°–170° C.

EXAMPLE 53 n-Butyl 3-{4-[1-(4-chlorobenzyl)-piperazin-4-yl]-phenyl}-propionate

A mixture of 20.0 g. (68.8 mmole) n-butyl 3-[4-(piperazin-1-yl)-phenyl]-propionate, 200 ml. acetonitrile, 10.4 g. (75.6 mmole) pulverised potassium carbonate and 12.2 g. (75.6 mmole) 4-chlorobenzyl chloride is heated for 36 hours at reflux temperature, filtered with suction and the filtrate evaporated. The residue is taken up in diethyl ether and the hydrochloride precipitated out by adding hydrogen chloride-containing diethyl ether. It is filtered off with suction, recrystallised from isopropanol and dried. Yield 29.0 g. (87% of theory) of hydrochloride; m.p. 222°–225° C.

EXAMPLE 54 n-Butyl 3-{4-[1-(4-chlorophenyl)-piperazin-4-yl]-phenyl}-propionate

A mixture of 12.3 g. (55 mmole) n-butyl 3-(4-aminophenyl)-propionate, 16.0 g. (55 mmole) N,N-bis-(2-chloroethyl)-4-chloroaniline and 50 ml. n-butanol is maintained at reflux temperature for 48 hours, then 3.8 g. (27 mmole) pulverised anhydrous potassium carbonate are added thereto and stirring continued for 1 week at reflux temperature. Thereafter, it is suction filtered hot, the filtrate is evaporated in a vacuum and the residue is stirred with ligroin and suction filtered. The product is now taken up in diethyl ether, filtered and mixed with hydrogen chloride-containing diethyl ether. Since the hydrochloride is difficult to suction filter, the ether phase is evaporated in a vacuum and the residue recrystallised from n-butanol. Yield 9.5 g. (39% of theory) of hydrochloride; m.p. 179°–183° C. (decomp.).

EXAMPLE 55 n-Butyl 3-{4-[1-(4-chlorocinnamoyl)-piperazin-4-yl]-phenyl}-propionate

To a solution of 15.8 g. (54 mmole) n-butyl 3-[4-(piperazin-1-yl)-phenyl]-propionate, 110 ml. methylene chloride and 8.2 g. (82 mmole) triethylamine is added dropwise at 0° to 5° C. a solution of 11.0 g. (54 mmole) 4-chlorocinnamoyl chloride in 50 ml. methylene chloride. Subsequently, the reaction mixture is stirred for 3 hours at 20° C.; then shaken out twice with water, dried with anhydrous magnesium sulphate and evaporated. After recrystallisation from n-butanol, the yield is 14.8 g. (60% of theory); m.p. 132°–133° C. The hydrochloride melts at 204°–207° C. The compound is light-sensitive.

The following compounds are prepared in an analogous manner:

(55a) ethyl 4-{2-[1-(2-methyl-3-phenylpropionyl)-piperazin-4-yl]-ethyl}-benzoate from ethyl 4-[2-(piperazin-1-yl)-ethyl]-benzoate dihydrochloride and 2-methyl-3-phenylpropionyl chloride.

Yield 96% of theory of oily base. The hydrochloride melts at 188°–189° C. (recrystallised from ethyl acetate)

(55b) ethyl 4-{3-[1-(4-chlorobenzoyl)-piperazin-4-yl]-propyl}-benzoate from ethyl 4-[3-(piperazin-1-yl)-propyl]-benzoate dihydrochloride and 4-chlorobenzoyl chloride Yield 70% of theory of hydrochloride monohydrate; m.p. 186°–187° C.

(55c) ethyl 4-{1-[1-(4-chlorobenzoyl)-piperazin-4-yl)-prop-2-yl}-benzoate from ethyl 4-[1-(piperazin-1-yl)-prop-2-yl]-benzoate dihydrochloride and 4-chlorobenzoyl chloride.

Yield 78% of theory of hydrochloride; m.p. 234°–235° C.

(recrystallised from ethanol).

EXAMPLE 56

By the reaction with acid chlorides or sulphonyl chlorides analogously to Example 47, from n-butyl 3-[4-(piperazin-1-yl)-phenyl]-propionate there are obtained the following products:

(56a) with 4-chlorobenzoyl chloride:

n-butyl 3-{4-[1-(4-chlorobenzoyl)-piperazin-4-yl]-phenyl}-propionate
Yield 65% of theory of hydrochloride; m.p. 186°-188° C.
(recrystallised from isopropanol)
(56b) with benzenesulphochloride:
n-butyl 3-{4-[1-(bennzenesulphonyl)-piperazin-4-yl]-phenyl}-propionate
Yield 69% of theory of hydrochloride; m.p. 197°-199° C.;
free base: m.p. 60°-62° C.

EXAMPLE 57

3-{4-[1-(2-Phenoxypropyl)-piperazin-4-yl]-phenyl}-propionic acid

A mixture of 15 g. (33 mmole) of the n-butyl ester, 100 ml. 1N aqueous sodium hydroxide solution and 100 ml. methanol is stirred for 6 hours at 60° C. The methanol is then distilled off, the isoelectric point is adjusted with hydrochloric acid and the precipitated smeary product is freed from water. It is dissolved in 6N hydrochloric acid, diluted with water and the precipitated crystals filtered off with suction. After recrystallisation from methanol, the yield of hydrochloride is 6.5 g. (43% of theory); m.p. 202°-204° C.

In an analogous manner, from the corresponding n-butyl esters; there are obtained:

(57a) 3-{4-[1-(4-chlorobenzyl)-piperazin-4-yl]-phenyl}-propionic acid
Yield 87% of theory of hydrochloride; m.p. 238°-240° C.

(57b) 3-{4-[1-(4-chlorobenzoyl)-piperazin-4-yl]-phenyl}-propionic acid
Yield 63% of theory; m.p. 162°-164° C. (recrystallised from methanol)

(57c) 3-{4-[1-(benzenesulphonyl)-piperazin-4-yl]-phenyl}-propionic acid
Yield 95% of theory of hydrochloride; m.p. 238°-239° C.

EXAMPLE 58

3-[4-(1-n-Hexadecylpiperazin-4-yl)-phenyl]-propionic acid

A mixture of 16.0 g. (30 mmole) n-butyl 3-[4-(1-n-hexadecylpiperazin-4-yl)-phenyl]-propionate, 125 ml. 1N aqueous sodium hydroxide solution and 125 ml. methanol is stirred for 6 hours at 60° C. and the methanol subsequently distilled off. Crystals precipitate out from the cold aqueous phase, which are filtered off with suction and washed with water. They are dissolved in hot water and the hydrochloride is precipitated with 2N hydrochloric acid. After suction filtration, washing with water and drying, the yield is 13.0 g. (85% of theory); m.p. 218°-220° C. When recrystallised from methanol, with the addition of a little water, the hydrochloride melts at 219°-221° C.

EXAMPLE 59

3-{4-[1-(4-Chlorophenyl)-piperazin-4-yl]-phenyl}-propionic acid

A mixture of 12.0 g. (27 mmole) of the n-butyl ester of the desired compound and 120 ml. 6N hydrochloric acid is maintained for 8 hours at reflux temperature, then cooled and the precipitated product filtered off with suction. After washing with dilute hydrochloric acid, 9.1 g. of the hydrochloride are obtained; m.p. 240°-242° C. (recrystallised from glacial acetic acid).

In an analogous manner, from the corresponding methyl ester, there is obtained 4-[2-(piperazin-1-yl)-propyl]-benzoic acid in the form of the dihydrochloride; m.p. 300° C. (recrystallised from methanol/4N hydrochloric acid). The yield is 88% of theory.

EXAMPLE 60

Ethyl 3-{4-[2-(piperazin-1-yl)-ethyl]-phenyl}-propionate (a) A mixture of 4.8 g. (20 mmole) 4'-(2-bromoethyl)-propiophenone, 3.5 g. (20 mmole) 1-benzylpiperazine, 5.5 g. (40 mmole) powdered anhydrous potassium carbonate and 100 ml. butan-2-one is maintained for 120 hours at reflux temperature, then suction filtered hot, the filter cake washed with acetone and the combined filtrates evaporated. The residue is freed from insolubles by dissolving in methanol and filtering, the methanol is then distilled off and the residue is taken up in diethyl ether. After repeated washing with water and drying with anhydrous sodium sulphate, the hydrochloride is precipitated out with hydrogen chloride-containing diethyl ether. It is filtered off with suction, washed with diethyl ether and dried. Yield 7.1 g. (87% of theory) 4'-[2-(1-benzylpiperazin-4-yl)-ethyl]-propiophenone as the hydrochloride; m.p. 280°-282° C. The free base melts at 51°-53° C.

(b) A mixture of 57.8 g. (172 mmole) 4'-[2-(1-benzylpiperazin-4-yl)-ethyl]-propionate, 14.35 g. (447 mmole) sulphur and 90.9 ml. morpholine is maintained for 120 hours at 140° C., then cooled and stirred into ice water, a plastic mass thereby being obtained, which is taken up in methylene chloride, washed three times with water and dried with anhydrous sodium sulphate. It is then evaporated, a quantitative yield of 3-{4-[2-(1-benzylpiperazin-4-yl)-ethyl]-phenyl}-propionic acid thiomorpholide remaining behind as a dark brown, non-crystallisable oil which is further worked up in crude form.

(c) 5.3 g. of the crude thiomorpholide are boiled with 15 ml. concentrated hydrochloric acid for 15 hours, then treated with active charcoal and filtered hot. After evaporation, the residue is triturated with some water, filtered off with suction and recrystallised from acetone to give 3.4 g. 3-{4-[2-(1-benzylpiperazin-4-yl)-ethyl]-phenyl}-propionic acid as the dihydrochloride; m.p. 246°-247° C.

(d) A boiling mixture of 117 g. (275 mmole) 4-{4-[2-(1-benzylpiperazin-4-yl)-ethyl]-phenyl}-propionic acid dihydrochloride and 1.2 liters anhydrous ethanol is slowly gassed with hydrogen chloride for 18 hours, then cooled and filtered off with suction to give 85.3 g. (69% of theory) ethyl 3-[4-[2-(1-benzylpiperazin-4-yl)-ethyl]-phenyl}-propionate dihydrochloride; m.p. 262°-264° C. (recrystallised from ethanol).

(e) A mixture of 57 g. (0.126 mole) ethyl 3-{4-[2-(1-benzylpiperazin-4-yl)-ethyl]-phenyl}-propionate and 200 ml. ethanol is hydrogenated, with the addition of 10% palladium-charcoal, at 50° C. and 50 bar hydrogen pressure in a shaking autoclave, then allowed to cool and filtered. After evaporation, the residue is dissolved in diethyl ether. The dihydrochloride is now precipitated out by adding hydrogen chloride-containing diethyl ether. The dihydrochloride is triturated with ethanol and filtered off with suction. Yield 31.0 g. (68% of theory) ethyl 3-{4-[2-(piperazin-1-yl)-ethyl]-phenyl}-propionate dihydrochloride; m.p. 243°-244° C.

EXAMPLE 61

4-Chlorobenzyl 3-{4-[2-(1-(4-chlorobenzyl)-piperazin-4-yl)-ethyl]-phenyl}-propionate This is obtained by reacting 3-{4-[2-(piperazin-1-yl)-ethyl]phenyl}-propionic acid (m.p. 264°–266° C.) with 2 mole 4-chlorobenzyl chloride analogously to Example 60a) (conditions potassium carbonate/butan-2-one; 36 hours reflux temperature). Yield 62% of theory of dihydrochloride; m.p. 248°–250° C.

EXAMPLE 62

Ethyl 3-{4-[2-(1-(4-methoxybenzyl)-piperazin-4-yl)-ethyl]-phenyl}-propionate This is obtained by reacting ethyl 3-{4-[2-(piperazin-1-yl)-ethyl]-phenyl}-propionate with 4-methoxybenzyl chloride analogously to Example (60a) in butan-2-one in the presence of potassium carbonate.
Reaction period: 36 hours. Yield 71% of theory of dihydrochloride; m.p. 262°–264° C. (recrystallised from aqueous ethanol).

EXAMPLE 63

Ethyl 3-{4-[2-(1-(4-chlorobenzoyl)-piperazin-4-yl)-ethyl]-phenyl}-propionate This is obtained analogously to Example 47 from 4-chlorobenzoylchloride and ethyl 3-{4-[2-(piperazin-1-yl)-ethyl]-phenyl}-propionate. Yield 80% of theory of hydrochloride; m.p. 222°–223° C. (recrystallised from ethanol).

Analogously thereto, with benzenesulphochloride there is obtained ethyl 3-{4-[2-(1-benzenesulphonylpiperazin-4-yl)-ethyl]-phenyl}-propionate; yield 91% of theory; m.p. 114°–116° C. (recrystallised from ethanol).

EXAMPLE 64

3-{4-[2-(1-(4-Chlorobenzyl)-piperazin-4-yl)-ethyl]-phenyl}-propionate

A mixture of 0.1 mole of the 4-chlorobenzyl ester of the desired compound, 0.3 mole 1N potassium hydroxide solution and an equal volume of methanol is maintained for 6 hours at 50° C. and then the methanol is distilled off. The aqueous alkaline phase is extracted with diethyl ether and then acidified with 2N hydrochloric acid. The product is filtered off with suction and the dried product is treated with hydrogen chloride-containing diethyl ether. Yield 83% of theory of dihydrochloride; m.p. 289°–290° C.

In analogous manner, from the corresponding ethyl esters, there are obtained the following acids:

(64a) 3-{4-[2-(1-(4-methoxybenzyl)-piperazin-4-yl)-ethyl]-phenyl}-propionic acid
yield 52% of theory of dihydrochloride; m.p. 277°–278° C.
(recrystallised from 2N hydrochloric acid)

(64b) 3-{4-[2-(1-(4-chlorobenzoyl)-piperazin-4-yl)-ethyl]-phenyl}-propionic acid
yield 76% of theory of hydrochloride; m.p. 249°–250° C.

(64 c) 3-{4-[2-(1-benzenesulphonylpiperazin-4-yl)-ethyl]-phenyl}-propionic acid
yield 95% of theory; m.p. 177°–178° C.; hydrochloride: m.p. 248°–249° C.

EXAMPLE 65

4-[1-(n-Hexadecyl)-piperazin-4-yl]-cinnamic acid (a) From n-hexadecyl bromide and ethyl 4-(piperazin-1-yl)-benzoate, there is obtained, analogously to Example (60 a), in a yield of 73%, ethyl 4-[1-(-n-hexadecyl)-piperazin-4-yl]-benzoate; m.p. 73°–75° C.

(b) By means of the lithium alanate reduction of ethyl 4-[1-(n-hexadecyl)-piperazin-4-yl]-benzoate in diethyl ether, there is obtained, in a yield of 72% of theory, 4-[1-(n-hexadecyl)-piperazin-4-yl]-benzyl alcohol; m.p. 101°–102° C.

(c) A mixture of 16.0 g. (38 mmole) of the above benzyl alcohol, 250 ml. methylene chloride and 15 g. manganese dioxide is stirred for 6 hours at 20° C., a further 8.5 g. manganese dioxide are added thereto, stirring continued for a further 5 hours and then filtered with suction. After evaporation of the filtrate in a vacuum, the residue is recrystallised once from ligroin and once from toluene to give 7.3 g. (46% of theory) 4-[1-(n-hexadecyl)-piperazin-4-yl]-benzaldehyde; m.p. 72°–73° C.

(d) A mixture of 10.0 g. (24 mmole) 4-[1-(n-hexadecyl)-piperazin-4-yl]-benzaldehyde, 2.51 g. (24 mmole) malonic acid, 50 ml. pyridine and 1.4 ml. piperidine is maintained for 3 hours at 90° C., then cooled, some diethyl ether added thereto and the product filtered off with suction. After washing with ligroin, the hydrochloride is prepared by means of hydrogen chloride-containing diethyl ether. For the removal of pyridine hydrochloride, the product is stirred with water, filtered with suction and dried. After recrystallisation from methanol, there are obtained 5.9 g. (47% of theory) 4-[1-(n-hexadecyl)-piperazin-4-yl]-cinnamic acid hydrochloride; m.p. 253°–254° C.

(65 a) In analogous manner, there are obtained: 4-[1-(2-phenoxypropyl)-piperazin-4-yl]-cinnamic acid via the following steps:

(a₁)ethyl 4-[1-(2-phenoxypropyl)-piperazin-4-yl]-benzoate
from 2-phenoxypropyl bromide and ethyl 4-(piperazin-1-yl)-benzoate
yield 54% of theory; m.p. of the hydrochloride: 199°–201° C.
(recrystallised from aqueous ethanol)

(b₁) 4-[1-(2-phenoxypropyl)-piperazin-4-yl]-benzyl alcohol by the lithium alanate reduction of the aldehyde,
yield 80% of theory; m.p. 82°–83° C.

(c₁-(2-phenoxypropyl)-piperazin-4-yl]-benzaldehyde by the oxidation of the benzyl alcohol with manganese oxide. Yield, 65% of colourless oil.

(d₁) A mixture of 9.0 g. (28 mmole) 4-[1-(2-phenoxypropyl)-piperazin-4-yl]-benzaldehyde, 2.9 g. (28 mmole) malonic acid, 40 ml. pyridine and 1.5 ml. piperidine is stirred for 3 hours at 90° C. The reaction mixture is then cooled, poured on to ice water and the oily product taken up with ethyl acetate. The solution is evaporated in a vacuum and the residue is dissolved in dilute aqueous sodium hydroxide solution and shaken out with ethyl acetate. The aqueouss phase is acidified with hydrochloric acid and the sparingly soluble hydrochloride is filtered off with suction and washed with water. After recrystallisation from methanol, there are obtained 7.0 g. (63% of theory)

4-[1-(2-phenoxypropyl)-piperazin-4-yl]-cinnamic acid hydrochloride; m.p. 208°-211° C.

EXAMPLE 66

4-[1-(n-Hexadecyl)piperazin-4-yl]-cinnamic acid 6.81 g. (48 mmole) Phosphorus pentoxide are suspended in 100 ml. methylene chloride, 15.2 g. (32 mmole) methyl 3-{4-[1-(n-hexadecyl)-piperazin-4-yl]-phenyl}-3-hydroxypropionate (colourless oil, prepared by the reduction of methyl 3-{4-[1-(n-hexadecyl)-piperazin-4-yl]-phenyl}-3-oxopropionate with sodium borohydride in methanol) are added thereto and the mixture is heated, with vigorous stirring, for 12 hours at reflux temperature. Subsequently, the smeary polyphosphoric acid is separated by decantation, the liquid phase is evaporated, the evaporation residue is dissolved in ethanol and, after the addition of 50 ml. 2N aqueous potassium hydroxide solution, the mixture is heated for 6 hours to 85° C. Subsequently, the ethanol is distilled off, the aqueous phase is extracted with diethyl ether and thereafter acidified with 6N hydrochloric acid. The precipitated product is filtered off with suction, washed with cold 2N hydrochloric acid and dried to give 8.8 g. (56% of theory) of the hydrochloride of the desired compound; m.p. 251°-253° C.

EXAMPLE 67

4-{2-[1-(4-Chlorocinnamyl)-piperazin-4-yl]-ethyl}-α-methylcinnamic acid (a) By the reaction of equimolar amounts of 1-(4-chlorocinnamyl)-piperazine with the glycol acetal of 4-(2-bromoethyl)-benzaldehyde analogously to Example 21, there is obtained, in a yield of 71% of theory, the glycol acetal of 4-{2-[1-4-chlorocinnamyl)-piperazin-4-yl]-ethyl}-benzaldehyde; m. p. 75°-77° C.

(b) A mixture of 25 g. (59.5 mmole) of the above-obtained glycol acetal, 500 ml. acetone, 10 ml. water and 59.5 ml. 2N hydrochloric acid is kept at reflux temperature for 2 hours and then evaporated. The crystalline residue is taken up in methylene chloride and the solution shaken out with 2N aqueous sodium carbonate solution. The solution is then washed with water, dried with anhydrous sodium sulphate and evaporated to give an almost quantitative yield of oily 4-{2-[1-(4-chlorocinnamyl)-piperazin-4-yl]-ethyl}-benzaldehyde; m.p. of the dihydrochloride 255°-258° C.

(c) To 2.92 g. (60 mmole) sodium hydride (as 50%) oil suspension) there is added dropwise at 20° C. a solution of 14.5 g. (60 mmole) 2-phosphonopropanoic acid triethyl ester and 50 ml. anhydrous 1,2-dimethoxyethane. The reaction mixture is then stirred for 10 minutes and subsequently a solution of 22.5 g. (60 mmole) 4-{2-[1-(4-chlorocinnamyl)-piperazin-4-yl]-ethyl}-benzaldehyde and 50 ml. anhydrous 1,2-dimethoxyethane added dropwise thereto, taking care that the temperature does not exceed 30° C. The reaction mixture is then stirred for 20 minutes at ambient temperature, about 50 ml. water are slowly added thereto and then it is extracted with diethyl ether. The ether phase is washed with water, dried with anhydrous sodium sulphate and evaporated to give 13.5 g. (49% of theory) of oily ethyl 4-{2-[1-4-chlorocinnamyl)-piperazin-4-yl]-ethyl}-α-methylcinnamate, the hydrochloride of which melts at 276°-280° C.

(d) A solution of 12.0 g. (26.5 mmole) of the above ethyl ester, 120 ml. ethanol and 55 ml 1N aqueous potassium hydroxide solution is stirred for 12 hours at ambient temperature. The reaction mixture is then evaporated to one third of its volume, 50 ml. water are added thereto and then it is extracted several times with diethyl ether, whereafter the aqueous phase is acidified with hydrochloric acid. The precipitate obtained is filtered off with suction and digested with hot diethyl ether. There are obtained 6.8 g. (52% of theory) of the dihydrochloride of 4-{2-[1-(4-chlorocinnamyl)-piperazin-4-yl]-ethyl}-α-methylcinnamic acid; m.p. 285°-287° C.

(67 a): 4-{2-[1-(4-Chlorobenzoyl)-piperazin-4-yl]-ethyl}-α-methylcinnamic acid is obtained in an analogous manner via the following intermediate stages:

($a_1$) 4-{2-[1-(4-chlorobenzoyl)-piperazin-4-yl]-ethyl}-benzaldehyde glycol acetal from 1-(4-chlorobenzoyl)-piperazine and 4-(2-bromoethyl)-benzaldehyde glycol acetal. Yield 70% of theory; m.p. 103°-104° C.

($b_1$) 4-{2-[1-(4-chlorobenzoyl)-piperazin-4-yl]-ethyl}-benzaldehyde from the above glycol acetal. Yield 91% of theory; m.p. 71°-73° C.

($c_1$) ethyl 4-{2-[1-(4-chlorobenzoyl)-piperazin-4-yl]-ethyl}-α-methylcinnamate from 4-{2-[1-(4-chlorobenzoyl)-piperazin-4-yl]-ethyl}-benzaldehyde and 2-phosphonopropanoic acid triethyl ester. Crude yield 95% of theory as a colourless oil; m.p. of the hydrochloride 235°-239° C.

($d_1$) By hydrolysis of the above ester, there is obtained the acid. Yield 50% of theory; hydrochloride: m.p. 275°-276° C. (recrystallised from ethanol).

EXAMPLE 68

4-{2-[1-(4-Chlorocinnamyl)-piperazin-4-yl]-ethyl}-β-methylcinnamic acid (a) By the reaction of 1-(4-chlorocinnamyl)-piperazine with 4-(2-bromoethyl)-acetophenone analogously to Example 22, there is obtained 4-{2-[1-(4-chlorocinnamyl)-piperazin-4-yl]-ethyl}-acetophenone. Yield 66% of theory of the dihydrochloride; m.p. 266°-267° C. (recrystallised from aqueous ethanol). The free base melts at 64°-65° C.

(b) To a solution of 1.0 g. (43 mg. atom) of sodium and 75 ml. anhydrous ethanol there are added 6.3 g. (28 mmole) phosphonoacetic acid triethyl ester. After allowing the reaction to proceed for 15 minutes, a solution of 10.8 g..(28 mmole) 4-{2-[1-(4-chlorocinnamyl)-piperazin-4-yl]-ethyl}-acetophenone and 50 ml. ethanol is added dropwise thereto. After standing for 24 hours at ambient temperature, the reaction mixture is evaporated, the residue is dissolved in diethyl ether and the ether phase is extracted twice with water. After drying with anhydrous sodium sulphate, the dihydrochloride is precipitated out with hydrogen chloride-containing diethyl ether. This is filtered off with suction, triturated with diethyl ether and recrystallised from hydrogen chloride-containing ethanol. There ae obtained 10.3 g. (70% of theory) of the dihydrochloride of ethyl 4-{2-[1-(4-chlorocinnamyl)-piperazin-4-yl]-ethyl}-β-methylcinnamate; m.p. 269°-271° C.

(c) A mixture of 9.3 g. (17.6 mmole) of the above ethyl ester dihydrochloride, 150 ml. ethanol and 50 ml. 2N aqueous sodium hydroxide solution is stirred at 45° C. until saponification is complete, whereafter the alcohol is distilled off in a vacuum. The solution is diluted with some water, extracted with ethyl acetate and finally acidified with hydrochloric acid. The product obtained is filtered off with suction, washed with water and acetone and recrystallised from dilute hydrochloric acid. There are obtained 6.2 g. (71% of theory) of the dihydrochloride of 4-{2-[1-(4-chlorocinnamyl)-piperazin-4-yl]-ethyl}-β-methylcinnamic acid; m.p. 271°–272° C.

Ethyl 4-{2-[1-(4-chlorobenzoyl)-piperazin-4-yl]-ethyl}-β-methylcinnamate is obtained analogously in the following way:

(a) By the reaction of 1-(4-chlorobenzoyl)-piperazine hydrochloride with 4-(2-bromoethyl)-acetophenone analogously to Example 22, there is obtained a yield of 62% of theory of the hydrochloride of 4-{2-[1-(4-chlorobenzoyl)-piperazin-4-yl]-ethyl}-acetophenone; m.p. 212°–214° C. The free base is a colourless oil.

(b) The desired product is obtained analogously to Example (68 b) from 4-{2-[1-(4-chlorobenzoyl)-piperazin-4-yl]-ethyl}-acetophenone and phosphonoacetic acid triethyl ester. The oily hydrochloride which precipitates out is brought into solution with a little acetone and then diethyl ether is added thereto, whereby crystallisation commences. There is obtained a yield of 67% of theory of the hydrochloride; m.p. 212°–215° C. (recrystallised from ethanol).

EXAMPLE 69

3-{4-{2-[1-(4-Chlorobenzoyl)-piperazin-4-yl]-ethyl}-phenyl}-butyric acid (a) By the reaction of 1-ethoxycarbonylpiperazine with 4-(2-bromoethyl)-acetophenone analogously to Example 22, there is obtained a yield of 69% of theory of 4-[2-(1-ethoxycarbonylpiperazin-4-yl)-ethyl]-acetophenone hydrochloride; m.p. 182°–185° C. (recrystallised from ethanol).

(b) From 4-[2-(1-ethoxycarbonylpiperazin-4-yl)-ethyl]-acetophenone and phosphonoacetic acid triethyl ester, there is obtained, analogously to Example (68 b), a yield of 63% of theory of the hydrochloride of ethyl 4-[2-(1-ethoxycarbonylpiperazin-4-yl)-ethyl]-β-methylcinnamate; m.p. 217°–218° C. (recrystallised from ethanol).

(c) A mixture of 25.0 g. (60 mmole) ethyl 4-[2-(1-ethoxycarbonylpiperazin-4-yl)-ethyl]-β-methylcinnamate hydrochloride, 500 ml. methanol, 75 ml. 2N hydrochloric acid and a spatula tip of 10% palladium-charcoal is hydrogenated at atmospheric pressure and ambient temperature, then filtered with suction and the filtrate evaporated. The residue is recrystallised from ethanol to give 14.3 g. (57% of theory) ethyl 3-{4-[2-(1-ethoxycarbonylpiperazin-4-yl)]ethyl]-phenyl}-butyrate hydrochloride; m.p. 220°–222° C.

(d) A mixture of 14.0 g. (34 mmole) ethyl 3-{4-[2-(1-ethoxycarbonylpiperazin-4-yl)-ethyl]-phenyl}-butyrate hydrochloride and 150 ml. concentrated hydrochloric acid is maintained for 12 hours at reflux temperature, then evaporated and the residue crystallised from acetone which contains some 2N hydrochloric acid. There are obtained 11.6 g. (98% of theory) of the dihydrochloride of 3-{4-[2-(piperazin-1-yl)-ethyl]-phenyl}-butyric acid; m.p. 231°–232° C.

(e) 11.4 g. of the dihydrochloride of 3-{4-[2-(piperazin-1-yl)-ethyl]-phenyl}-butyric acid are dissolved in 120 ml. ethanol and gassed for 2 hours at reflux temperature with hydrogen chloride. The reaction mixture is then evaporated to one half its volume, cooled, mixed with diethyl ether and filtered with suction. There are obtained 10.8 g. (88% of theory) of the dihydrochloride of ethyl 3-{4-[2-(piperazin-1-yl)-ethyl]-phenyl}-butyrate; m.p. 249°–251° C. (recrystallised from ethanol).

(f) By the reaction of the above ethyl butyrate with 4-chlorobenzoyl chloride analogously to Example 55, there is obtained a yield of 94% of theory of the hydrochloride of ethyl 3-{4-{2-[1-(4-chlorobenzoyl)-piperazin-4-yl]-ethyl}-phenyl}-butyrate; m.p. 189°–191° C. (recrystallised from ethanol).

(g) The desired final product is obtained by hydrolysing ethyl 3-{4-{2-[1-(4-chlorobenzoyl)-piperazin-4-yl]-ethyl}-phenyl}-butyrate with a mixture of 2N aqueous sodium hydroxide solution and ethanol analogously to Example 64. After the addition of hydrochloric acid, the product contains 4-chlorobenzoic acid, which is removed by stirring with diethyl ether. The hydrochloride of the desired product is obtained in a yield of 60% of theory; m.p. 249°–251° C. (recrystallised from ethanol).

EXAMPLE 70

4-{2-[1-(4-Carboxycinnamyl)-piperazin-4-yl]-ethyl}-benzoic acid

A mixture of ethyl 4-{2-[1-(4-cyanocinnamyl)-piperazin-4-yl]-ethyl}-benzoate and a solution of equal volumes of 10N aqueous sodium hydroxide solution and ethanol is heated for 3 hours in an autoclave to 130° C. and the ethanol subsequently evaporated off. It is then acidified with concentrated hydrochloric acid, strongly cooled and the precipitate obtained filtered off with suction. After recrystallisation from water, there is obtained the dihydrochloride of the desired compound in a yield of 47% of theory; m.p. 274°–276° C.

EXAMPLE 71

1-(4-Carboxyphenethyl)-4-[2-(4-carboxyphenoxy)-propyl]-piperazine

A mixture of 7.5 g. (15 mmole) 1-(4-ethoxycarbonylphenethyl)-4-[2-(4-cyanophenoxy)-propyl]-piperazine dihydrochloride and 75 ml. concentrated hydrochloric acid is kept for 12 hours at reflux temperature and then cooled, suction filtered and the product obtained recrystallised from 1N hydrochloric acid. There are obtained 5.2 g. (70% of theory) of the dihydrochloride of the desired compound; m.p. 270°–271° C.

EXAMPLE 72

1-(4-Carboxyphenethyl)-4-[2-(4-acetaminophenoxy)-propyl]-piperazine

A mixture of 9.3 g. (18.9 mmole) 1-(4-carboxyphenethyl)-4-[2-(4-aminophenoxy)-propyl]-piperazine trihydrochloride and 50 ml. acetic anhydride is kept for 2 hours at 100° C. and then cooled. The precipitate obtained is filtered off with suction and recrystallised from acetic acid. There are obtained 8.2 g. (87% of theory) of the desired compound in the form of a dihydrochloride; m.p. 234°–235° C.

EXAMPLE 73

1-(4-Ethoxycarbonylphenethyl)-4-[2-(4-aminophenoxy)-propyl]-piperazine 1-(4-Ethoxycarbonylphenethyl)-4-[2-(4-nitrophenoxy)-propyl]-piperazine dihydrochloride in ethanol is hydrogenated in the presence of 10% palladium-charcoal, with the addition of 10% by volume of 2N hydrochloric acid, at atmospheric pressure. The catalyst is then filtered off, the filtrate is evaporated in a vacuum and the residue is triturated with cold ethanol. The desired product is obtained as the dihydrochloride in a yield of 80% of theory; m.p. 260°–261° C.

EXAMPLE 74

4-{2-[1-(3-Chlorobenzyl)-piperazin-4-yl]-ethyl}-benzoic acid diethylamide

A mixture of 5.0 g. (11 mmole) 4-{2-[1-(3-chlorobenzyl)-piperazin-4-yl]-ethyl}-benzoic acid dihydrochloride, 50 ml. thionyl chloride and 2 drops of dimethyl formamide is kept for 4 hours at reflux temperature, then cooled and suction filtered. The acid chloride thus obtained is washed with anhydrous diethyl ether, dissolved in tetrahydrofuran and 8.1 g. (0.11 mole) diethylamine added thereto. After stirring for 30 minutes, the diethylamine hydrochloride is filtered off with suction and the filtrate evaporated. The residue is taken up in diethyl ether and the solution mixed with hydrogen chloride-containing diethyl ether. The precipitated dihydrochloride is filtered off with suction and recrystallised from a mixture of ethanol and 2N hydrochloric acid. There are obtained 3.6 g. (66% of theory) of the desired compound in the form of its dihydrochloride; m.p. 251°–252° C.

EXAMPLE 75

4-{2-[1-(2-Chlorobenzyl)-piperazin-4-yl]-ethyl}-benzoic acid 2-hydroxyethylamide To a solution of 11.0 g. (24.4 mmole) 4-{2-[1-(2-chlorobenzyl)-piperazin-4-yl]-ethyl}-benzoyl chloride dihydrochloride (prepared from the dihydrochloride of the acid by boiling for 3 hours with excess thionyl chloride, evaporating and digesting with ligroin; yield 98% of theory; m.p. 260° C.) and 10 ml. anhydrous pyridine there are added, with stirring at 20° C., 10 ml. ethanolamine and the reaction mixture is left to stand overnight and then poured into about 100 ml. water. The precipitate obtained is washed with an aqueous solution of sodium bicarbonate and with water, dried and then recrystallised from aqueous ethanol. There is obtained a yield of the desired product of 5.0 g. (51% of theory); m.p. 121°–122° C.

EXAMPLE 76

4-{2-[1-(2-Chlorobenzyl)-piperazin-4-yl]-ethyl}-benzoic acid amide

To a solution of 14.2 g. (31.5 mmole) 4-{2-[1-(2-chlorobenzyl)-piperazin-4-yl]-ethyl}-benzoyl chloride dihydrochloride and 150 ml. dioxan, there is added dropwise, while stirring at ambient temperature, within the course of 30 minutes, a solution of 100 ml. concentrated aqueous ammonia in 50 ml. dioxan. The reaction mixture is stirred for a further 30 minutes and then sufficient water is added thereto to precipitate out the desired amide. After suction filtration, drying and recrystallisation from toluene, there are obtained 8.5 g. (75% of theory) of amide; m.p. 170°–173° C.

EXAMPLE 77

2-Diethylaminoethyl 4-{2-[1-(2-chlorobenzyl)-piperazin-4-yl]-ethyl}-benzoate

A mixture of 9.45 g. (21 mmole) 4-{2-[1-(2-chlorobenzyl)-piperazin-4-yl]-ethyl}-benzoyl chloride dihydrochloride, 50 ml. methylene chloride and 3.3 g. (28 mmole) 2-diethylaminoethanol is maintained at reflux temperature for 3 hours, then cooled and mixed with diethyl ether until turbidity appears. A thick precipitate is slowly deposited. This is filtered off with suction, washed with sec.-butanol and dissolved in a hot mixture of sec.-butanol and ethanol. Upon cooling and partial concentration, there are obtained 5.0 g. (35% of theory) of the desired compound in the form of its dihydrochloride; m.p. 220°–221° C.

EXAMPLE 78

4-{1-[1-(4-Chlorocinnamyl)-piperazin-4-yl]-prop-2-yl}-benzoic acid (a) By the reaction of 1-benzylpiperazine with ethyl 4-(1-bromoprop-2-yl)-benzoate analogously to Example 23, there is obtained a yield of 80% of theory of ethyl 4-[1-(1-benzylpiperazin-4-yl)-prop-2-yl]-benzoate as dihydrochloride; m.p. 235°–236° C. (recrystallised from ethanol).

(b) Hydrogenation of the compound obtained according to (a) under the conditions described in Example (20 b) gives a yield of 62% of theory of the dihydrochloride of ethyl 4-[1-(piperazin-1-yl)-prop-2-yl]-benzoate; m.p. 245°–246° C. (recrystallised from aqueous ethanol).

(c) By the reaction of 4-chlorocinnamyl chloride with the dihydrochloride of 4-[1-(piperazin-1-yl)-prop-2-yl]-benzoate in methylene chloride in the presence of triethylamine (analogously to Example 25), there is obtained a yield of 81% of theory of the dihydrochloride of ethyl 4-{1-[1-(4-chlorocinnamyl)-piperazin-4-yl]-prop-2-yl}-benzoate; m.p. 249°–250° C. (recrystallised from ethanol).

(d) The desired final product is obtained by saponifying for 16 hours the ethyl ester obtained in (c) above with aqueous hydrochloric acid at boiling temperature, analogously to Example 34. The product is obtained as the dihydrochloride in a yield of 64% of theory; m.p. 290°–291° C. (recrystallised from glacial acetic acid).

EXAMPLE 79

4-{2-[1-(4-Chlorocinnamyl)-piperazin-4-yl]-propyl}-benzoic acid (a) To a mixture of 15.5 g. (88 mmole) 1-benzylpiperazine and 200 ml. anhydrous methanol, there is added sufficient hydrogen chloride-containing methanol to give a pH value of 5. 15.3 g. (80 mmole) methyl 4-(2-oxopropyl)-benzoate and 3.5 g. (55 mmole) sodium cyanoborohydride are then added thereto and the reaction mixture is stirred for 4 days at ambient temperature and mixed with concentrated hydrochloric acid. By fractional precipitation with diethyl ether, there are obtained 19.2 g. (57% of theory) of the dihydrochloride of methyl 4-[2-(1-benzylpiperazin-4-yl)-propyl]-benzoate; m.p. 256° C.

(b) The benzyl compound obtained in (a) above is hydrogenated in methanolic solution in the presence of palladium-charcoal at 50° C. and atmospheric pressure and the product obtained is recrystallised from methanol. There is obtained a yield of 76% of theory of the dihydrochloride of methyl 4-[2-(piperazin-1-yl)-propyl]-benzoate; m.p. 238° C.

(c) By the reaction of the free methyl 4-[2-(piperazin-1-yl)-propyl]-benzoate with 3-chlorocinnamyl chloride in butan-2-one in the presence of potassium carbonate (analogously to Example 23) there is obtained methyl 4-{2-[1-(4-chlorocinnamyl)-piperazin-4-yl]-propyl}-benzoate. The yield of the dihydrochloride is 71% of theory; m.p. 263° C. (recrystallised from methanol/2N hydrochloric acid).

(d) By hydrolysis of the methyl ester obtained in (c) above analogously to Example 64, there is obtained the desired compound in the form of its dihydrochloride in a yield of 84% of theory; m.p. 286° C. (recrystallised from ethanol/2N hydrochloric acid).

EXAMPLE 80

Tablets are prepared, each of which contains 20 mg. of 4-{2-[1-(2-phenoxypropyl)-piperazin-4-yl]-ethyl}-benzoic acid, according to the following formulation:

| 4-{2-[1-(2-phenoxypropyl)-piperazin-4-yl]-ethyl}-benzoic acid | 20 g. |
|---|---|
| lactose | 160 g. |
| starch | 158 g. |
| magnesium stearate | 2 g. |

The active compound is finely pulverised and mixed with the lactose and starch. The mixture obtained is granulated in conventional manner. Magnesium stearate is then added to the granulate and the mixture is pressed to give 1000 tablets, each weighing 0.24 g.

To show the lipid lowering and thrombocyte aggregation inhibiting action of the compounds of the invention the following experiments were performed:

1. Lowering of Lipid Levels

In each case, 10 male rats of normal metabolism were administered the test substance for 7 days in a dosage of 100 mg/kg/d in methyl cellulose suspension. At the end of the experiment, 3 hours after the last does was administered, the cholesterol and triglyceride levels in the serum were determined. The changes are given in Table I expressed as a percentage in comparison to control for a representative selection of compounds.

| | Lipide level reduction | |
|---|---|---|
| Example No. | % of reduction of cholesterol | % of reduction of triglycerides |
| 33 r | 33 | 15 |
| 33 u | 28 | 32 |
| 34 i | 21 | 10 |
| 34 s | 47 | 21 |
| 55 b | 33 | 3 |
| 67 d$_1$ | 37 | 9 |
| 50 g | 28 | 9 |
| 13 i | 38 | 15 |
| 33 f | 37 | 42 |
| 33 l | 38 | 22 |
| 33 c | 13 | 11 |
| 33 i | 41 | 24 |
| 33 o | 35 | 13 |
| 34 c | 30 | 40 |
| 33 d | 43 | 41 |
| 49 e | 41 | 8 |
| 50 f | 40 | 16 |
| 33 m | 20 | 30 |
| 50 o | 26 | 14 |
| 58 | 17 | 6 |
| 33 b | 40 | 30 |
| 50 j | 40 | 0 |
| 65 d$_1$ | 5 | 20 |

2. Inhibition of Aggregation

The effect on thrombocyte aggregation was determined by the Born test (J. Physiol. 168, 178, 1963) using human blood samples.

(a) Method

Venous blood from subjects of normal metabolism is mixed with sodium citrate (9:1). The erythrocytes are settled by centrifugation at 150 g. The thrombocytes are concentrated in the supernatant. This supernatant is referred to as platelet-rich plasma (PRP). An aliquot of the PRP is placed in the cell of an aggregometer (Universal Aggregometer mfd. by Braun Melsungen) and there stirred by means of a small magnet. The substance to be tested is added in an aqueous solution (pH approx. 7). Changes in the light transmission in the suspension are continuously registered by a recorder. After spontaneous aggregation ends, aggregation is triggered by the addition of adrenalin (end concentration $5 \times 10^{-6}$ mol/l). Larger clumps of thrombocytes form and this causes the transmission of light through the suspension to increase.

(b) Evaluation

The adrenalin-induced aggregation takes place in two phases, i.e., the light transmission first increases, then briefly remains steady, and then again increases. Only the second phase of the aggregation can be influenced by aggregation inhibitors.

To document the findings, the angle of the second aggregation phase with respect to the horizontal representing the aggregation induced by adrenalin is determined and this is taken to be 0% inhibition. (Control test).

With the same PRP, aggregation is induced with adrenalin after addition of the test substance and the course of the aggregation is registered with the recorder. The angle of the 2nd phase from the horizontal is again determined and the ratio of the two angles gives the percentage of inhibition of the 2nd phase of the thrombocyte aggregation.

(For the acetylsalicylic acid used as the standard, which has good aggregation inhibiting effect, the inhibition at a concentration of $10^{-4}$ mol/l is 100%. At a concentration of $5 \times 10^{-5}$ mol/l it is 0%.)

All substances were tested in a concentration of $14^{-4}$ mol/l in determining their aggregation inhibiting action.

The results are summed up in Table II:

| Example | % of inhibition of thrombocyte aggregation |
|---|---|
| 34 i | 100 |
| 33 c | 40 |
| 34 c | 7 |
| 33 d | 6 |
| 33 b | 19 |

It will be understood that the specification and examples are illustrative but not limiative of the present invention and that other embodiments within the spirit and scope of the invention will suggest themselves to those skilled in the art.

What is claimed is:

1. A carboxylic acid compound of the formula:

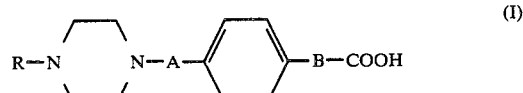

(I)

wherein

A is a valency bond or a saturated branched or straight-chained lower alkylene chain having 1 to 3 carbon atoms, B is a valency bond, a saturated lower aliphatic chain having 1 to 3 carbon atoms or an unsaturated lower aliphatic chain having 2 or 3 carbon atoms, and R is a hydrogen atom, a straight-chained or branched alkyl group with 1 to 16 carbon atoms, a straight-chained or branched alkyl group with 1 to 3 carbon atoms substituted up to three times by substituents individually selected from the group consisting of hydroxyl, carboxyl, sulphonic acid, 3,5-di-tert-butyl-4-hydroxyphenoxy, phenoxy or phenoxy substituted by a substituent individually selected from the group consisting of $C_1-C_6$ lower alkyl, $C_1-C_6$ lower alkoxy, halogen, nitro, cyano, carboxyl or acetylamino residue; or R is a phenylalkyl group, or a 3,5-di-tert-butyl-4-hydroxyphenylalkyl group or a phenylalkyl group the phenyl part being substituted by a substituent individually selected from the group consisting of halogen, hydroxyl, $C_1-C_6$ lower alkoxy, cyano, carboxyl, nitro, acetylamino residue, $C_1-C_6$ lower alkyl or trifluoromethyl and wherein the alkyl part of which is saturated or unsaturated and has up to 4 carbon atoms; or R is a phenacyl group or a phenacyl group the phenyl part of which is substituted by halogen, hydroxyl or $C_1-C_6$ lower alkyl; or R is 2-methyl-3-phenylpropionyl, 3-phenylpropionyl, cinnamoyl, phenacetyl, benzoyl, the phenyl group being the 3,5-di-tert-butyl-4-hydroxyphenyl group or being unsubstituted or substituted by a substituent individually selected from the group consisting of halogen, hydroxyl or $C_1-C_6$ lower alkyl, or an acyl group derived from methane-sulphonic acid, benzenesulphonic acid or phenacylsulphonic acid; or R is a phenyl group or a phenyl group substituted by halogen, trifluoromethyl, phenyl, phenoxy, benzyloxy, 4-chlorobenzyl or 4-chlorophenoxy;

with the proviso that when A is a valency bond, R cannot be hydrogen, methyl, ethyl, hydroxyethyl, benzyl or phenyl; and a physiologically acceptable salt, ester or amide thereof formed at the B-COOH carboxyl group, wherein the amides are simple or $C_1-C_6$ lower alkyl or hydroxy lower amides and the esters are $C_1-C_6$ lower alkyl, $C_2-C_{12}$ di-lower alkyl, amino $C_1-C_6$ lower alkyl or benzyl.

2. Compound according to claim 1, wherein A is a valency bond.

3. Compound according to claim 1, wherein A is the lower alkylene chain.

4. Compound of claim 1 or 3 wherein B is a methylene group.

5. Compound of claim 1 wherein B is an ethylene group.

6. Compound of claim 1 or 3 wherein B is a valency bond.

7. Compound of claim 1 wherein B is a saturated or unsaturated lower aliphatic chain.

8. Compound of claim 1 wherein R is a hydrogen atom, a straight-chained or branched alkyl group with 1 to 16 carbon atoms or $C_1-C_3$ alkyl group substituted up to three times by substituents individually selected from the group consisting of hydroxy, carboxyl, sulphonic acid, 3,5-di-tert-butyl-4-hydroxyphenoxy, phenoxy or phenoxy substituted by a $C_1-C_6$ lower alkyl, $C_1-C_6$ lower alkoxy, halogen, nitro, cyano, carboxyl or acetylamino residue.

9. Compound of claim 1 wherein R is a phenylalkyl group, a 3,5-di-tert-butyl-4-hydroxyphenylalkyl group or a phenylalkyl group the phenyl moiety of which is substituted with a substituent individually selected from the group consisting of halogen, hydroxyl, $C_1-C_6$ lower alkoxy, cyano, carboxyl, nitro, acetylamino residue, $C_1-C_6$ lower alkyl or trifluoromethyl, and wherein the alkyl moiety of which is saturated or unsaturated and has up to 4 carbon atoms.

10. Compound of claim 1 wherein R is a phenacyl group or a phenacyl group the phenyl moiety of which is substituted by a halogen, a hydroxyl or a $C_1-C_6$ lower alkyl.

11. Compound of claim 1 wherein R is an acyl group derived from an aliphatic, araliphatic or aromatic carboxylic or sulphonic acid, the aryl group being the 3,5-di-tert-butyl-4-hydroxyphenyl group, or being unsubstituted or substituted by a halogen, a hydroxyl or a $C_1-C_6$ lower alkyl.

12. Compound of claim 1 wherein R is the aryl group, which can be substituted by halogen, trifluoromethyl, phenyl, phenoxy, benzyloxy, 4-chlorobenzoyl or 4-chlorophenoxy.

13. Compound of claim 1 wherein R is the alkyl group with 1 to 16 carbon atoms.

14. Compound of claim 1 wherein R is a hydrogen atom.

15. Compound of claim 1 wherein R is the substituted alkyl group with 1 to 3 carbon atoms.

16. Compound of claim 1 designated 1-(4-carboxyphenethyl)-4-[2-(4-nitrophenoxy)-propyl]piperazine.

17. Compound of claim 1 designated 4-{2-[1-(2-chlorobenzyl)-piperazin-4-yl]-ethyl}-benzoic acid.

18. Compound of claim 1 designated 4-{2-[1-(2-(4-methoxyphenoxy)-propyl)-piperazin-4-yl]-ethyl}-benzoic acid.

19. Compound of claim 1 designated 4-{2-[1-(4-chlorocinnamyl)-piperazin-4-yl]-ethyl}-benzoic acid.

20. Compound of claim 1 designated 4-{2-[1-(2-phenoxypropyl)-piperazin-4-yl]-ethyl}-benzoic acid.

21. Composition for depressing lipids, which composition comprises a pharmacologically acceptable carrier and, in effective amounts, the compound claimed in claim 1.

22. Composition for inhibiting thrombocyte aggregation which composition comprises a pharmacologically acceptable carrier and, in effective amounts the compound claimed in claim 1.

* * * * *

UNITED STATES PATENT AND TRADEMARK OFFICE
CERTIFICATE OF CORRECTION

PATENT NO. : 4,616,086

DATED : October 7, 1986

INVENTOR(S) : Ernst Christian Witte, et al.

Page 1 of 2

It is certified that error appears in the above-identified patent and that said Letters Patent is hereby corrected as shown below:

Title: delete "Useful For Treating Infirmities Caused By Excess Lipids or Thrombocyte".

Column 8, line 39: change "Raformatzky" to -- Reformatzky --.

Column 12, line 8: change "hydroscopic" to -- hygroscopic --.

Column 36, line 34: change "133" to -- 233 --.

Column 41, line 7: change "bennzenesulphonyl" to -- benzenesulphonyl --.

Column 44, line 52: change "($C_1$-(2-phenoxy propyl" to -- $C_1$)-4-[1-(2-phenoxypropyl --.

Column 45, line 34: change "1-4" to -- (1-(4 --.

Column 45, line 61: change "1-4" to -- (1-(4 --.

UNITED STATES PATENT AND TRADEMARK OFFICE
CERTIFICATE OF CORRECTION

PATENT NO. : 4,616,086

DATED : October 7, 1986

INVENTOR(S) Ernst Christian Witte, et al

It is certified that error appears in the above-identified patent and that said Letters Patent is hereby corrected as shown below:

Column 46, line 55: change "ae" to -- are --.

Signed and Sealed this

Thirteenth Day of October, 1987

Attest:

DONALD J. QUIGG

*Attesting Officer*  *Commissioner of Patents and Trademarks*